(12) United States Patent
Seto et al.

(10) Patent No.: US 9,402,946 B2
(45) Date of Patent: Aug. 2, 2016

(54) LIQUID EJECTING APPARATUS

(71) Applicant: SEIKO EPSON CORPORATION, Tokyo (JP)

(72) Inventors: Takeshi Seto, Chofu (JP); Hirokazu Sekino, Chino (JP); Kazuaki Uchida, Matsumoto (JP); Kazuo Kawasumi, Chino (JP)

(73) Assignee: Seiko Epson Corporation, Tokyo (JP)

( * ) Notice: Subject to any disclaimer, the term of this patent is extended or adjusted under 35 U.S.C. 154(b) by 0 days.

(21) Appl. No.: 14/550,418

(22) Filed: Nov. 21, 2014

(65) Prior Publication Data

US 2015/0075367 A1    Mar. 19, 2015

Related U.S. Application Data

(63) Continuation of application No. 13/352,164, filed on Jan. 17, 2012, now Pat. No. 8,919,664.

(30) Foreign Application Priority Data

| Jan. 18, 2011 | (JP) | 2011-007555 |
| Jan. 24, 2011 | (JP) | 2011-011684 |
| Sep. 8, 2011 | (JP) | 2011-195742 |
| Sep. 8, 2011 | (JP) | 2011-195749 |
| Sep. 8, 2011 | (JP) | 2011-195750 |

(51) Int. Cl.
*B05B 1/08* (2006.01)
*A61M 3/02* (2006.01)
(Continued)

(52) U.S. Cl.
CPC .............. *A61M 3/02* (2013.01); *A61B 17/3203* (2013.01); *F04B 43/02* (2013.01)

(58) Field of Classification Search
CPC . F02M 47/022; F02M 47/025; F02M 47/027; F02M 63/0022; F02M 63/0075
USPC .............. 239/533.9, 585.1, 585.3, 585.4, 584
See application file for complete search history.

(56) References Cited

U.S. PATENT DOCUMENTS

| 3,504,893 A | 4/1970 | Hiroshi et al. |
| 4,702,418 A | 10/1987 | Carter et al. |

(Continued)

FOREIGN PATENT DOCUMENTS

| EP | 1905590 | 4/2008 |
| JP | 05-079459 | 3/1993 |

(Continued)

OTHER PUBLICATIONS

European Search Report for European Patent Application No. 12151368.3 dated Jan. 8, 2014.

(Continued)

*Primary Examiner* — Davis Hwu
(74) *Attorney, Agent, or Firm* — Workman Nydegger

(57) ABSTRACT

A liquid ejecting apparatus includes: an inflow channel to which liquid is supplied; an outflow channel communicated with a nozzle; a liquid chamber formed with a spiral flow channel having a substantially constant cross-sectional area between the inflow channel and the outflow channel and having a given volume; a volume changing portion configured to deform the liquid chamber so as to change the volume of the liquid chamber to a volume smaller than the given volume; and an ejection control unit configured to cause the liquid to be ejected from the nozzle in a pulsed manner by driving the volume changing portion in a state in which the liquid chamber is filled with the liquid.

14 Claims, 16 Drawing Sheets

(51) Int. Cl.
*A61B 17/3203* (2006.01)
*F04B 43/02* (2006.01)

(56) References Cited

U.S. PATENT DOCUMENTS

| | | | |
|---|---|---|---|
| 6,419,167 B1 | 7/2002 | Fuchs | |
| 6,923,383 B1 | 8/2005 | Joshi et al. | |
| 7,407,120 B1* | 8/2008 | French | F02M 51/0675 239/585.5 |
| 7,600,987 B2 | 10/2009 | Seto et al. | |
| 7,901,374 B2 | 3/2011 | Seto et al. | |
| 2006/0169803 A1* | 8/2006 | Kanamori | F02M 47/027 239/533.3 |
| 2007/0170286 A1* | 7/2007 | Boecking | F02M 47/027 239/533.2 |
| 2010/0054960 A1 | 3/2010 | Seto et al. | |
| 2010/0078495 A1 | 4/2010 | Seto et al. | |

FOREIGN PATENT DOCUMENTS

| | | |
|---|---|---|
| JP | 2001-342963 | 12/2001 |
| JP | 2007-138814 | 6/2007 |
| JP | 2008-082202 | 4/2008 |
| JP | 2010-059902 | 3/2010 |
| JP | 2011-058504 | 3/2011 |

OTHER PUBLICATIONS

U.S. Appl. No. 13/352,164, Aug. 22, 2014, Notice of Allowance.

* cited by examiner

LIQUID EJECTING APPARATUS

CROSS REFERENCES TO RELATED APPLICATIONS

This application is a Continuation of U.S. patent application Ser. No. 13/352,164 filed Jan. 17, 2012, which is expressly incorporated herein by reference in its entirety. U.S. patent application Ser. No. 13/352,164 claims the benefit of each of the following Japanese Patent applications, and each of the following Japanese Patent applications are incorporated herein by reference in their entirety:
1. Japanese Patent Application No. 2011-007555, filed Jan. 18, 2011;
2. Japanese Patent Application No. 2011-011684, filed Jan. 24, 2011;
3. Japanese Patent Application No. 2011-195742, filed Sep. 8, 2011;
4. Japanese Patent Application No. 2011-195749, filed Sep. 8, 2011
5. Japanese Patent Application No. 2011-195750, filed Sep. 8, 2011.

BACKGROUND

1. Technical Field

The present invention relates to a liquid ejecting apparatus.

2. Related Art

There is developed a liquid ejecting apparatus configured to incise or excise living tissues by pressurizing liquid such as water or physiologic saline and ejecting the liquid toward the living tissues from a nozzle that has a reduced cross-sectional area. A surgical operation using such a liquid ejecting apparatus enables incision or excision of living tissues such as internal organs exclusively and selectively without damaging nerves, blood vessels or the like, and causes less damage to peripheral tissues. Therefore, burdens on patients can be reduced.

In addition, there is proposed a liquid ejecting apparatus which enables incision and excision of living tissues with a small ejecting amount by causing liquid to be ejected in a pulsed manner instead of simply causing the liquid to be ejected continuously from a nozzle (for example, see JP-A-2008-082202). Such a liquid ejecting apparatus is configured to abruptly raise the pressure in a liquid chamber that is filled with liquid by abruptly reducing the volume of the liquid chamber. This causes the liquid to be ejected from a nozzle connected to the liquid chamber in a pulsed manner using the increased pressure. Subsequently, the volume of the liquid chamber is restored and the liquid chamber is again filled. By repeating such actions, a pulsed jet stream is cyclically generated.

However, such a liquid ejecting apparatus configured to eject liquid in a pulsed manner suffers in that incising and excising performance tends to deteriorate due to accumulation of air bubbles existing in the liquid or air bubbles generated from air dissolved in the liquid under certain conditions in the liquid chamber. In other words, as described above, since a pulsed jet stream is generated by pressurizing the liquid in the liquid chamber by reducing the volume of the liquid chamber, if there exists air bubbles in the liquid chamber, the liquid cannot be pressurized sufficiently because such air bubbles are compressed when the volume of the liquid chamber is reduced. Therefore, the pulsed ejection of liquid from the nozzle cannot be achieved, and hence the incising and excising performances are disadvantageously lowered.

SUMMARY

An advantage of some aspects of the invention is to solve at least a part of the problems described above, and the invention can be implemented as the following forms or application examples.

Application Example 1

This application example of the invention is directed to a liquid ejecting apparatus including: an inflow channel to which liquid is supplied; an outflow channel communicated with a nozzle; a liquid chamber formed with a spiral flow channel having a substantially constant cross-sectional area between the inflow channel and the outflow channel and having a given volume; a volume changing portion configured to deform the liquid chamber so as to change the volume of the liquid chamber to a volume smaller than the given volume; and an ejection control unit configured to cause the liquid to be ejected from the nozzle in a pulsed manner by driving the volume changing portion in a state in which the liquid chamber is filled with the liquid.

In this configuration, the liquid chamber having the spiral-shaped flow channel is formed between the inflow channel and the outflow channel and, when the volume changing portion is driven, the liquid chamber is pressed by the volume changing portion and the volume of the liquid chamber is reduced. Consequently, the liquid in the liquid chamber is quickly pressurized, and hence high-velocity ejection of pressurized liquid from the nozzle communicating with the outflow channel of the liquid chamber is achieved.

The liquid ejecting apparatus is configured to avoid easy accumulation of air bubbles in the liquid chamber because the liquid supplied from the inflow channel flows toward the outflow channel along the spiral flow channel when filing the liquid chamber with liquid.

For example, when the flow of the liquid in the liquid chamber is irregular and there are variations in flow velocity, the air bubbles tend to accumulate in a portion flowing at a low velocity and the liquid cannot be pressurized sufficiently by the existence of these air bubbles. Consequently, adequate ejection of the liquid cannot be achieved. Therefore, by forming the spiral flow channel having a substantially constant cross-sectional area between the inflow channel and the outflow channel, the flow of the liquid in the liquid chamber is restricted to a substantially constant velocity along the spiral flow channel. Therefore, accumulation of air bubbles in a portion where the flow of liquid is slow is inhibited, and hence the air bubbles in the liquid chamber can be discharged easily from the outflow channel. Consequently, the pressure in the liquid chamber can be increased sufficiently without being affected by the air bubbles and hence stable ejection of liquid can be maintained.

Application Example 2

In the liquid ejecting apparatus of the above application example, it is preferred that the volume changing portion includes a piezoelectric element, the volume of the liquid chamber is reduced by an expansion of the piezoelectric element, and the piezoelectric element is disposed so as to press the liquid chamber in a state that the piezoelectric element does not extend/expand.

Here, the piezoelectric element expands and reduces the volume of the liquid chamber when being applied with a drive voltage waveform from the ejection control unit, and contracts and restores the volume of the liquid chamber to a given volume when the application of the drive voltage waveform is released.

The piezoelectric element which reduces the volume of the liquid chamber by expanding has such property as being resistant to a force of compression applied from the outside, but is vulnerable to a force of tension. Therefore, when the force of tension is applied to the piezoelectric element, the piezoelectric element may have damage. Accordingly, by providing the piezoelectric element so as to press the liquid chamber also in a state in which the piezoelectric element is not expanded, the force in the direction of compression can be kept acting on the piezoelectric element in advance as a reaction force of the pressure applied to the liquid chamber. Consequently, when a force in the pulling direction is applied to the piezoelectric element, the force in the pulling direction is alleviated, and hence the probability of occurrence of damage of the piezoelectric element due to the action of tensile force is reduced.

Furthermore, by providing the piezoelectric element so as to keep the liquid chamber to be pressed by the piezoelectric element also in a state in which the piezoelectric element is not expanded, the pressing of the liquid chamber is immediately started when the piezoelectric element starts to expand. Therefore, the liquid ejection is efficiently performed without causing any stroke loss between the expansion of the piezoelectric element and the reduction in volume of the liquid chamber.

Application Example 3

In the liquid ejecting apparatus of the above application example, it is preferred that the cross-sectional area of the inflow channel is smaller than the cross-sectional area of the outflow channel, and the inflow channel has a capillary shape.

When the volume of the liquid chamber is reduced, the liquid is urged to be flowed out from both of the outflow channel and the inflow channel. However since the inflow channel has a cross-sectional area smaller than the cross-sectional area of the outflow channel and has a capillary shape, the pressure in the liquid chamber can be increased while inhibiting backflow of the liquid to the inflow channel, whereby an outflow from the outflow channel having a large cross-sectional area can be facilitated. In this configuration, the backflow can be inhibited even when a check valve or the like is not provided in the inflow channel. The term "capillary shape" of the inflow channel means a thin tube having a flow channel diameter on the order of 0.3 mm, which will be described in embodiments later.

Application Example 4

In the liquid ejecting apparatus of the above application example, it is preferred that the liquid ejecting apparatus includes an ejection unit including the inflow channel, the outflow channel, the liquid chamber, and the nozzle; and a volume changing unit including the volume changing portion, and the ejection unit and the volume changing unit are detachable attachable.

The ejecting unit is an element which causes liquid such as water, salt water, or medical solution to flow, and may come into contact with blood or body fluid when the liquid ejecting apparatus is used as an surgical operation tool. Therefore, by configuring the ejecting unit to be capable of being removed from the volume changing unit as a disposable unit, higher security is ensured.

In contrast, the volume changing unit which does not come into contact with the liquid can be used repeatedly. Since the volume changing unit is costly in comparison with the ejecting unit, the running cost can be reduced by using the volume changing unit repeatedly.

Application Example 5

In the liquid ejecting apparatus of the above application example, it is preferred that the liquid chamber is a flexible tube wound into a spiral shape, and the tube includes an inlet port communicated with the inflow channel and an outlet port communicated with the outflow channel.

In the configuration in which the liquid chamber is formed of the tube having the inlet port and the outlet port, the layout of the inflow channel and the outflow channel or the wound shape of the tube is not restricted. Therefore, flexibility in design of the liquid chamber is increased, and hence simplification of the structure of the liquid ejecting apparatus or miniaturization of the same is achieved.

Also, by using the tube, the cross-sectional area of the spiral flow channel can be kept to be substantially constant easily.

Application Example 6

In the liquid ejecting apparatus of the above application example, it is preferred that the tube includes a gap between each of adjacent turns.

The term "between each of adjacent turns" means between a first turn and a second turn, between the second turn and a third turn, and so forth.

The volume of the tube is changed by being pressed by the volume changing portion. In this case, by the provision of the gap by an amount corresponding to the deformation, increase in load by pressing the adjacent turns of the tube to each other is eliminated, and the pressing amount required for ejecting liquid can be ensured.

Application Example 7

In the liquid ejecting apparatus of the above application example, it is preferred that the inlet port is arranged at an outer-peripheral-side end of the tube wound into a spiral shape, and the outlet port is arranged at a center-side end of the tube wound into the spiral shape.

In the liquid ejecting apparatus configured in this manner, the pressing force in the vicinity of the center of the liquid chamber tends to be stronger than the pressing force in the peripheral portion. Therefore, since the pressure directed toward the outflow channel is increased, the liquid can be pushed out strongly.

In such configuration, the inflow channel communicated with the inlet port is arranged on the outer-peripheral-side end and the outflow channel communicated with the outlet port is arranged on the center-side end. Therefore, when operating the liquid ejecting apparatus while holding with hand, the nozzle located on an extension of the outflow channel can be arranged at a substantially center of the liquid ejecting apparatus, so that an advantage of easy-to-operate is achieved.

Application Example 8

In the liquid ejecting apparatus of the above application example, it is preferred that the inlet port is arranged at the center-side end of the tube wound into the spiral shape, and the outlet port is arranged at the outer-peripheral-side end of the tube wound into the spiral shape.

As described above, when the tube is pressed by the piezoelectric element, the pressing amount with respect to the center portion tends to be larger than the pressing amount with respect to the outer peripheral portion. Therefore, by arranging the inlet port at the center portion, the pressure in the vicinity of the inlet port is increased. In this case, by employing a capillary shape for the inlet port (inflow channel) so as to have cross-sectional areas, which is smaller than that of the outlet port (outflow channel), a backflow from the liquid chamber to the inlet port is inhibited. Therefore, the pressure in the liquid chamber can be increased, and hence a strong liquid ejection is achieved.

Application Example 9

In the liquid ejecting apparatus of the above application example, it is preferred that the liquid chamber is partitioned into the spiral-shaped flow channel having a substantially constant cross section area by a flexible partitioning wall between the inflow channel and the outflow channel.

When the volume changing portion is driven in a state in which in the liquid chamber is filled with the liquid supplied from the inflow channel, the partitioning wall is deformed and hence the volume of the liquid chamber is reduced. Consequently, the liquid pressurized in the liquid chamber flows along the spiral-shaped flow channel and guided to the outflow channel, and is ejected from the nozzle through the outflow channel. Therefore, with the configuration in this application example, since the liquid flows at a sufficiently high flow velocity along the spiral-shaped flow channel, accumulation of air bubbles at a portion in which the flow of liquid is slow is inhibited, so that the air bubbles in the liquid chamber can be discharged quickly from the outflow channel. Consequently, the pressure in the liquid chamber can be increased sufficiently without being affected by the air bubbles and hence stable ejection of liquid can be performed.

When the volume of the liquid chamber is reduced upon driving of the volume changing portion, the partitioning wall is deformed so as to cause the flow channel to contract toward the outflow channel. Therefore, the pressurized liquid in the liquid chamber can be moved toward the outflow channel and ejected strongly.

Application Example 10

In the liquid ejecting apparatus of the above application example, it is preferred that the partitioning wall extends upright from one of a surface on the side of a first direction and a surface on the side of a second direction, the surface on the side of the first direction constituting the liquid chamber and configured to reduce the volume of the liquid chamber to a volume smaller than the given volume and the surface on the side of the second direction opposing the surface on the side of the first direction, and the partitioning wall is provided in a state in which a distal end portion opposing the surface on the second direction or a distal end portion opposing the first direction is not fixed.

In this configuration, when the volume of the liquid chamber is reduced upon driving of the volume changing portion, the distal end portion of the partitioning wall which is not fixed can be deformed so as to be inclined toward the outflow channel. Therefore, a flow of liquid directed toward the outflow channel beyond the partitioning wall can be generated in the interior of the liquid chamber. In this manner, since the liquid is collected to the outflow channel from the periphery together with the flow flowing across the spiral-shaped flow channel, the liquid can be ejected adequately.

Application Example 11

In the liquid ejecting apparatus of the above application example, it is preferred that the partitioning wall extends upright from one of a surface on the side of a first direction and a surface on the side of a second direction, the surface on the side of the first direction constituting the liquid chamber and configured to reduce the volume of the liquid chamber to a volume smaller than the given volume and the surface on the side of the second direction opposing the surface on the side of the first direction, and the portion of the partitioning wall other than an outermost peripheral side of the partitioning wall is provided in a state in which a distal end portion opposing the surface on the first direction and a distal end portion opposing the second direction are not fixed.

The partitioning wall in this configuration may be considered to have a fixed wall on the outermost peripheral side and a movable wall on the inner peripheral side. When the volume of the liquid chamber is reduced upon driving of the volume changing portion, the partitioning wall on the inner peripheral side, which is the movable wall, is deformed so as to move toward the outflow channel, and hence the liquid in the liquid chamber can be moved from the inflow channel toward the outflow channel of the liquid chamber.

Application Example 12

In the liquid ejecting apparatus of the above application example, it is preferred that the inflow channel is communicated with the outer-peripheral-side end of the spiral flow channel of the liquid chamber, and the outflow channel is communicated with the center-side end of the spiral flow channel of the liquid chamber.

In this configuration, when the liquid chamber is formed into the spiral shape by the partitioning wall, in the configuration in which the distal end of the partitioning wall is fixed, the pressure is directed from the outer periphery toward the center portion, and hence the center portion of the partitioning wall in the direction of the section is deformed toward the center where the outflow channel exists.

In the configuration in which the distal end of the partitioning wall is not fixed, the distal end side of the partitioning wall is deformed, and a flow of liquid flowing from the outer periphery toward the center beyond the partitioning wall is generated. Therefore, the liquid can be collected from the outer periphery toward the outflow channel, so that the liquid can be ejected strongly.

When the partitioning wall on the inner peripheral side is the movable wall, the partitioning wall is deformed so as to move toward the center portion as if winding the spring, so that the liquid can be collected to the center portion.

Application Example 13

In the liquid ejecting apparatus of the above application example, it is preferred that the inflow channel is communicated with the center-side end of the spiral flow channel of the liquid chamber, and the outflow channel is communicated with the outer-peripheral-side end of the spiral flow channel of the liquid chamber.

In this configuration, when the liquid chamber is formed into the spiral shape by the partitioning wall, in the configuration in which the distal end of the partitioning wall is fixed, the pressure is directed from the center portion where the inflow channel is arranged toward the outer periphery, the center portion of the partitioning wall in the direction of the section is deformed toward the outer periphery where the outflow channel exists. Also, in the configuration in which the distal end portion of the partitioning wall is not fixed, the distal end portion of the partitioning wall is deformed toward the outer periphery, and a flow of liquid flowing from the center where the inflow channel is arranged toward the outer periphery where the outflow channel is arranged beyond the partitioning wall is generated. Therefore, the liquid can be collected from the periphery toward the outflow channel, so that the liquid can be ejected strongly.

When the partitioning wall on the inner peripheral side is the movable wall, the partitioning wall is deformed so as to move toward the outer periphery as if the spring is released, so that the liquid can be collected to the outflow channel.

In addition, as described above, since the liquid is pumped from the center portion to the outflow channel at the outer peripheral portion, air-bubble eliminating capability is further enhanced.

BRIEF DESCRIPTION OF THE DRAWINGS

The invention will be described with reference to the accompanying drawings, wherein like numbers reference like elements.

DESCRIPTION OF EXEMPLARY EMBODIMENTS

Referring now to drawings, embodiments of the invention will be described below.

Drawings referred to in the description given below are schematic drawings in which members may not be drawn to scale vertical or horizontally for purposes of illustrating respective members in recognizable sizes.

Liquid Ejecting Apparatus

First, a configuration of a liquid ejecting apparatus 10 will be described.

Figure 1:
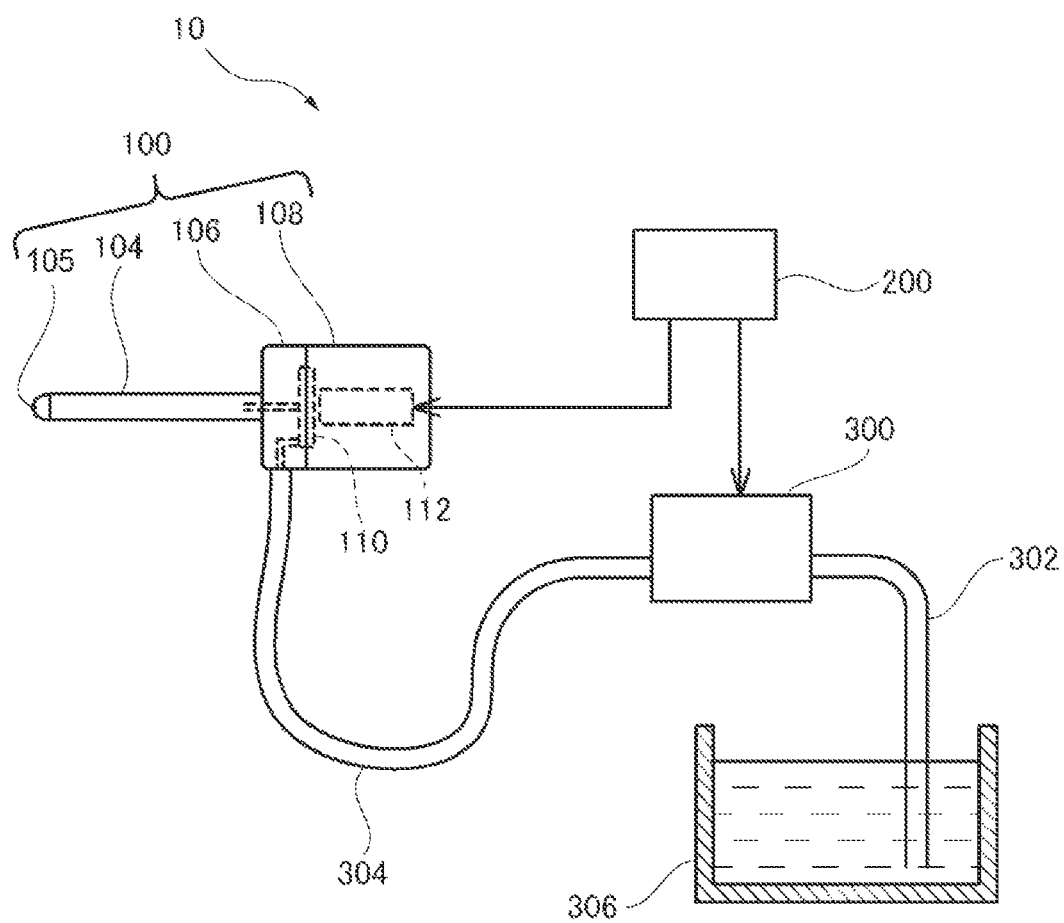
FIG. 1 is an explanatory drawing showing a principal configuration of a liquid ejecting apparatus.

FIG. 1 is an explanatory drawing showing a principal configuration of the liquid ejecting apparatus 10. The liquid ejecting apparatus 10 includes a pulsation generator 100 configured to eject liquid such as water or physiologic saline in a pulsed manner, a liquid supply unit 300 configured to supply the liquid to the pulsation generator 100, a liquid container 306 configured to store the liquid to be ejected, and a control unit 200 as an ejection controller configured to control actions of the pulsation generator 100 and the liquid supply unit 300.

The pulsation generator 100 has a structure including a second case 106 and a first case 108 mating each other and demountably fixed to each other by screw clamping or the like. A cylindrical liquid ejecting tube 104 is connected to a surface of the second case 106 opposite from a mating surface with respect to the first case 108 and a nozzle 105 is provided at a distal end of the liquid ejecting tube 104.

Provided on the mating surface between the second case 106 and the first case 108 is a liquid chamber 110 in which the liquid is to be filled. The liquid chamber 110 is connected to the nozzle 105 via the liquid ejecting tube 104. Provided in the interior of the first case 108 is a laminated piezoelectric element 112, which enables pulsed ejection of the liquid in the liquid chamber 110 from the nozzle 105 by varying the volume of the liquid chamber 110 by applying a drive voltage waveform from the control unit 200 to the piezoelectric element 112 to cause expansion and contraction thereof. Detailed configurations of the pulsation generator 100 will be described later with reference to FIG. 2.

The liquid supply unit 300 is connected to a liquid container 306 via a first connecting tube 302 and configured to supply liquid drawn from the liquid container 306 to the liquid chamber 110 of the pulsation generator 100 via a second connecting tube 304. The liquid supply unit 300 in this embodiment, not illustrated, has a configuration in which two pistons slide in cylinders, and is capable of pumping the liquid stably toward the pulsation generator 100 by adequately controlling the velocity of movement of the both pistons.

The control unit 200 controls the action of the piezoelectric element 112 that is integrated in the pulsation generator 100 and controls the action of the liquid supply unit 300. In the liquid ejecting apparatus 10 according to this embodiment, the mode of ejection of the liquid from the nozzle 105 can be varied by changing the flow rate of the liquid to be supplied from the liquid supply unit 300, the drive voltage waveform to be applied to the piezoelectric element 112, and the maximum voltage value and the frequency.

Subsequently, the configuration of the pulsation generator 100 will be described with reference to representative embodiments.

First Embodiment

Figure 2:
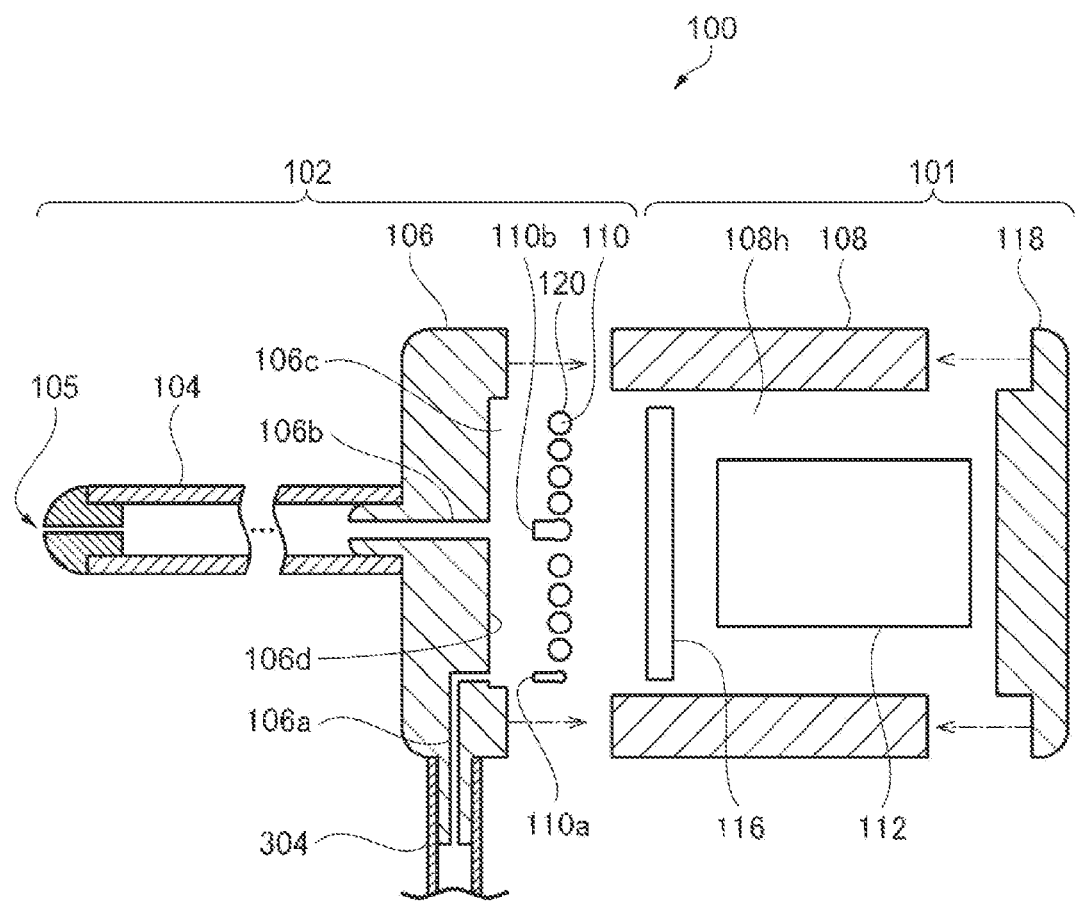
FIG. 2 is an exploded view showing an assembly of a pulsation generator according to a first embodiment.

FIG. 2 is an exploded view showing an assembly of the pulsation generator 100 according to a first embodiment. The pulsation generator 100 includes the second case 106 and the first case 108 mated together and fixed to each other by screw clamping. Therefore, the second case 106 and the first case 108 are detachable. The first case 108 is formed with a through hole 108h penetrating through the first case 108 and having a circular cross-section and at a center position of a plane mated with the second case 106. The piezoelectric element 112 is accommodated in the through hole 108h and an opening of the through hole 108h on the opposite side from the mating surface with respect to the second case 106 is covered with a third case 118. The piezoelectric element 112 is formed of a laminated piezoelectric element, which is formed by laminating a number of piezoelectric bodies into a column shape, and an end of the piezoelectric element 112 is fixed to the third case 118. A circular reinforcing plate 116 formed of a metal plate is secured to the other end of the piezoelectric element 112. In this embodiment, a combination of the piezoelectric element 112 and the reinforcing plate 116 corresponds to a "volume changing portion" and it reduces the volume of the liquid chamber 110.

The second case 106 is formed with a circular shallow depression 106c on the mating surface with respect to the first case 108. Formed at a position of a peripheral edge of the depression 106c is an inflow channel 106a which communicates with the second connecting tube 304 connected to the second case 106. Formed at a substantially center of the depression 106c is an outflow channel 106b which communicates with the liquid ejecting tube 104.

The liquid chamber 110 (formed of a tube 120 having a circular cross section) is arranged in the depression 106c of the second case 106. In the pulsation generator 100 of this embodiment, the liquid chamber 110 is formed of a metallic tube. However, the material of the tube 120 is not specifically limited to the metal as long as it has flexibility, and a resin-made tube may also be used. Also, the cross-sectional shape of the tube 120 is not limited to a circular shape, as a square shape and an oval shape may also be used.

Figure 3:
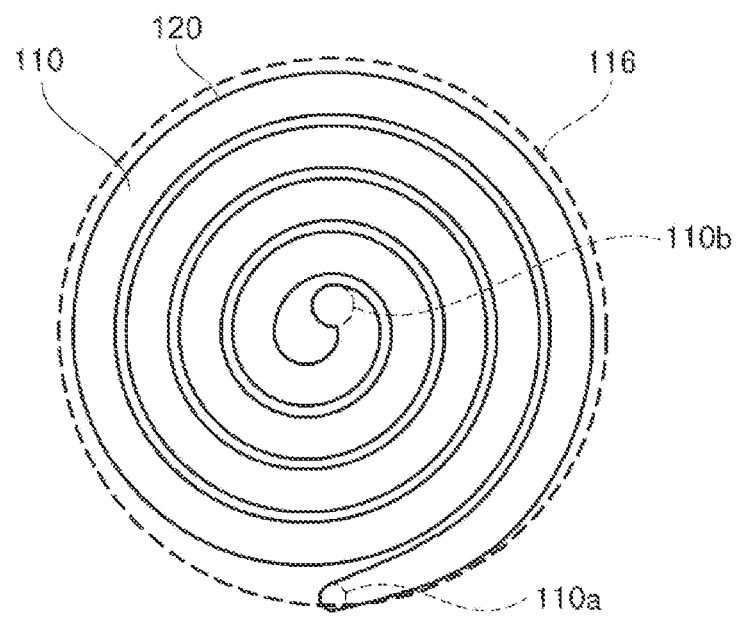
FIG. 3 is an explanatory drawing showing a configuration of a liquid chamber according to the first embodiment.

Referring now to FIG. 3, the configuration of the liquid chamber 110 will be described.

FIG. 3 is an explanatory drawing showing the configuration of the liquid chamber 110 according to the first embodiment. In FIG. 3, a state of the liquid chamber 110 viewed from the side of the first case 108 is shown. As illustrated, the liquid chamber 110 is formed into a substantially circular shape by winding the tube 120 into a spiral shape. A predetermined gap is formed between each of adjacent turns of the tube 120.

The diameter of the outermost periphery of the spiral-shaped tube 120 is set to be smaller than the outer diameter of the circular reinforcing plate 116. Furthermore, an outer peripheral side end and a center-side end of the tube 120 are bent toward the second case 106 (see FIG. 2). In this embodiment, an opening at the outer peripheral side end of the spiral-shaped tube 120 which forms the liquid chamber 110 is referred to as an "inlet port 110a" and an opening at the center-side end thereof is referred to as an "outlet port 110b".

The liquid chamber 110 configured in this manner is installed in the depression 106c of the second case 106 in a state in which the inlet port 110a is connected to the inflow channel 106a, and the outlet port 110b is connected to the outflow channel 106b as shown in FIG. 2. When mating and securing the second case 106 and the first case 108 with screw clamping, the surface of the tube 120 on one side comes into contact with a depression bottom 106d of the second case 106, and the surface of the tube 120 on the other side comes into contact with the reinforcing plate 116, so that the tube 120 is brought into a state of being sandwiched between the depression bottom 106d and the reinforcing plate 116.

As described above, the tube 120 is in abutment with the depression bottom 106d of the second case 106 on one side, and is in abutment with the reinforcing plate 116 on the other side. Although detailed description is given later, in the case of the pulsation generator 100 in this embodiment, the thickness or the like of the reinforcing plate 116 is set so that the piezoelectric element 112 keeps a state of pressing the side surface of the tube 120 via the reinforcing plate 116 even in a state in which the drive voltage waveform is not applied and hence the piezoelectric element 112 is not expanded. However, the pressing amount in this case may be smaller than a pressing amount achieved when the drive voltage waveform is applied and hence the piezoelectric element 112 is expanded, which just brings the reinforcing plate 116 to come into contact with the tube 120 without forming a gap therebetween.

As shown in FIG. 2, the liquid ejecting tube 104 is connected to the second case 106 on the surface opposite from the mating surface with respect to the first case 108. The inner diameter of the liquid ejecting tube 104 is set to be larger than the inner diameter of the outflow channel 106b. Also, the nozzle 105 having a liquid ejecting opening set to have an inner diameter smaller than that of the outflow channel 106b is fitted by insertion to the distal end of the liquid ejecting tube 104. Therefore, the cross-sectional area of a flow channel for allowing passage of liquid pressurized in the liquid chamber 110 is increased in the liquid ejecting tube 104 after the outflow channel 106b and then narrowed again at the nozzle 105 at the distal end of the liquid ejecting tube 104.

Here, a configuration including the first case 108, the third case 118, the piezoelectric element 112, and the reinforcing plate 116 secured to each other is referred to as a volume changing unit 101. A configuration including the second case 106, the liquid ejecting tube 104 (including the nozzle 105), and the tube 120 are secured to each other or fixed by insertion is referred to as an ejecting unit 102.

The volume changing unit 101 and the ejecting unit 102 are configured to be demountably mounted by screw fixation or the like along the mating surface between the first case 108 and the second case 106.

With the pulsation generator 100 configured as described above, pulsated ejection of the liquid from the nozzle 105 is achieved by applying the drive voltage waveform on the piezoelectric element 112 and causing expansion and contraction thereof. Subsequently, an action of the liquid generator 100 ejecting the liquid will be described.

Figure 4A:
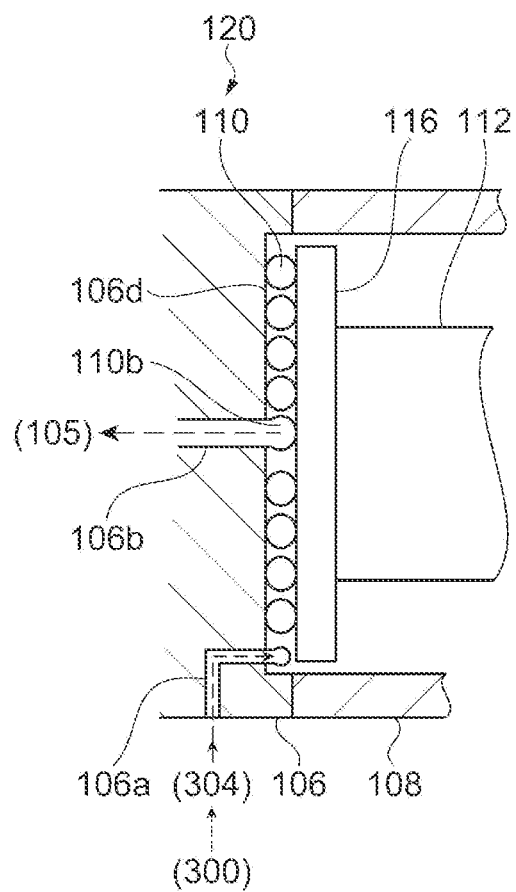
FIG. 4A is an explanatory drawing partly in cross section showing the pulsation generator in a state in which a drive voltage waveform is not applied to a piezoelectric element.
Figure 4B:
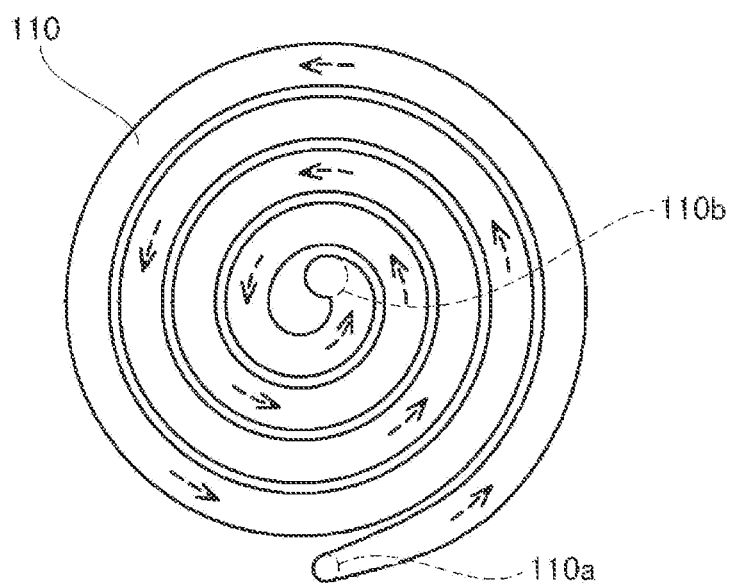
FIG. 4B is an explanatory plan view of the liquid chamber in a state in which the drive voltage waveform is not applied to the piezoelectric element.
Figure 5A:
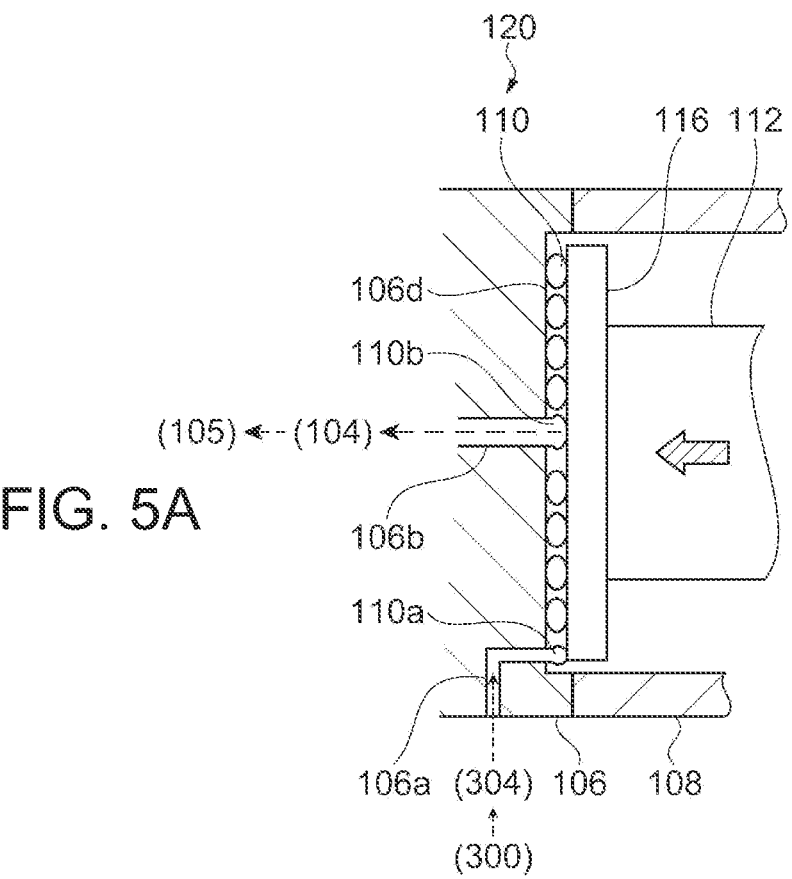
FIG. 5A is an explanatory drawing partly in cross section showing the pulsation generator in a state in which the drive voltage waveform is applied to the piezoelectric element.
Figure 5B:
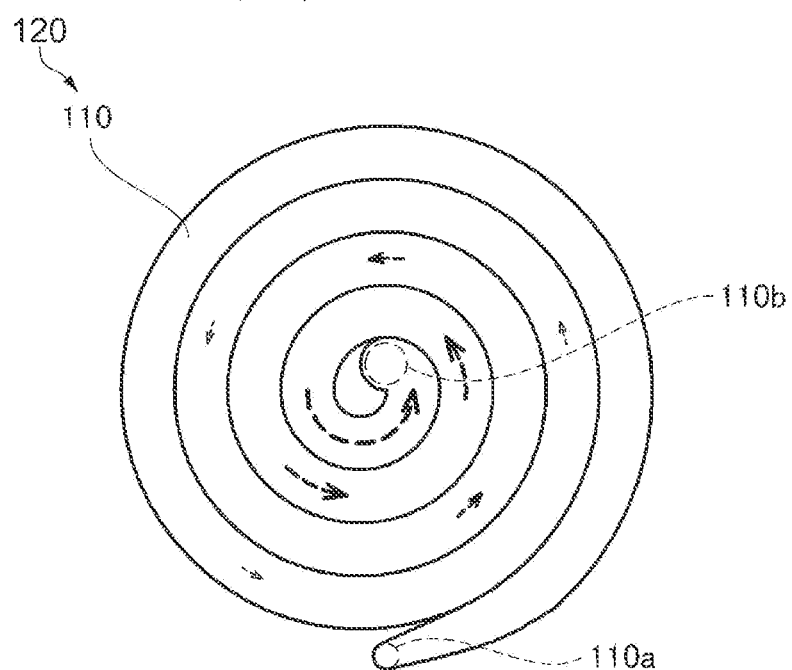
FIG. 5B is an explanatory plan view of the liquid chamber in a state in which the drive voltage waveform is applied to the piezoelectric element.

FIGS. 4A and 4B and FIGS. 5A and 5B are explanatory drawings schematically showing a liquid ejecting action of pulsation generator 100 in the first embodiment. FIGS. 4A and 4B show a state in which the drive voltage waveform is not applied to the piezoelectric element 112, and FIGS. 5A and 5B show a state in which the drive voltage waveform is applied to the piezoelectric element 112.

Referring now to FIGS. 4A and 4B, a state in which the piezoelectric element 112 is not driven will be described. FIG. 4A is a partly cross-sectional view of the pulsation generator 100, and FIG. 4B is a plan view of the liquid chamber 110. In this state, as shown in FIG. 4A, liquid to be supplied from the liquid supply unit 300 via the second connecting tube 304 to the pulsation generator 100 passes through the inflow channel 106a and flows into the liquid chamber 110, and the liquid chamber 110 is filled with the liquid. An arrow in broken line in FIG. 4A shows a flow of liquid.

As show in FIG. 4B, the liquid chamber 110 is formed with a spiral flow channel by the tube 120 wound into a spiral shape. Liquid flowing from the inlet port 110a on the periphery thereof connected to the inflow channel 106a turns along the tube 120 and is guided to the outlet port 110b at the center connected to the outflow channel 106b. Indicated by arrows of a broken line in FIG. 4B is the flow of the liquid. Since the cross-sectional area of the spiral flow channel of the tube 120 is substantially constant, the liquid in the liquid chamber 110 can be flowed at a substantially constant velocity from the inlet port 110a to the outlet port 110b.

As described above, since the liquid is supplied from the liquid supply unit 300 at a constant and stabilized pressure, when the liquid chamber 110 is filled with liquid, the liquid in the liquid chamber 110 is pushed out from the outlet port 110b through the outflow channel 106b toward the nozzle 105 even when the piezoelectric element 112 is not driven.

Referring now to FIGS. 5A and 5B, a state in which the piezoelectric element 112 is driven will be described. FIG. 5A is a partly cross-sectional view of the pulsation generator 100, and FIG. 5B is a plan view of the liquid chamber 110.

When the drive voltage waveform is applied to the piezoelectric element 112 in a state in which he liquid chamber 110 is filled with liquid, the piezoelectric element 112 is expanded by an increased drive voltage and presses the side surface of the tube 120 toward the depression bottom 106d of the second case 106 via the reinforcing plate 116 as shown in FIG. 5A. Therefore, the cross section of the tube 120 is deformed from a circular shape to an oval shape, and the volume of the liquid chamber 110 is reduced. Consequently, the liquid in the liquid chamber 110 is pressurized.

Since the diameter of the outermost periphery of the tube 120 which forms the liquid chamber 110 is set to be smaller than the outer diameter of the reinforcing plate 116, the entire spiral flow channel of the liquid chamber 110 is brought into a pressed state. The tube 120 is wound with a predetermined gap formed between each of adjacent turns. However, when the tube 120 is pressed and deformed, the tube 120 is brought into a state of being in tight contact with each other or a state in which the gaps are reduced. The liquid pressurized in the liquid chamber 110 in this manner is ejected from the nozzle 105 via the outflow channel 106b connected to the outlet port 110b and the liquid ejecting tube 104 as shown by an arrow of a broken line in FIG. 5A.

Two channels, namely, the inflow channel 106a connected to the inlet port 110a and the outflow channel 106b connected to the outlet port 110b are connected to the liquid chamber 110. Therefore, the liquid pressurized in the liquid chamber 110 is considered to flow out not only to the outflow channel 106b, but also to the inflow channel 106a. However, transmissibility of the liquid in the flow channel is determined by the cross-sectional area of the flow channel, the length of the flow channel, or the like. For example, when a capillary shape having a diameter of the outlet port 110b to be on the order of 1 mm and a diameter of the flow channel of the inlet port 110a to be on the order of 0.3 mm is employed, the change of the flow rate per unit time is proportional to the cross-sectional area and is inversely proportional to the length. Therefore, most of the liquid can flow out to the outflow channel 106b.

In addition, since the liquid pumped from the liquid supply unit 300 tries to enter the liquid chamber 110 through the inflow channel 106a, a backflow of the liquid in the liquid chamber 110 is prevented. Few elements resist the outflow of the liquid in the liquid chamber 110 or increase the inertia exist in the outflow channel 106b. Therefore, the liquid pressurized in the liquid chamber 110 exclusively flows out to the outflow channel 106b and is ejected from the nozzle 105 at the distal end thereof via the liquid ejecting tube 104.

As shown in FIG. 5B, the spiral flow channel of the liquid chamber 110 is formed by winding the tube 120 in a spiral shape, and the liquid pressurized in the liquid chamber 110 moves to the outlet port 110b at the center along the spiral-shaped tube 120. At this time, in a portion of an outermost periphery of the spiral tube 120 that is distant from the central outlet port 110b, the liquid flux is small. However, the flow rate is increased as the liquid approaches the outlet port 110b and, at a portion close to the outlet port 110b, the liquid corresponding to the amount of reduction of volume of the liquid chamber 110 moves abruptly and pushed out from the outlet port 110b. Consequently, the liquid is ejected at a high velocity from the nozzle 105 via the outflow channel 106b and the liquid ejecting tube 104.

When the drive voltage is subsequently lowered, the piezoelectric element 112 contracts and is restored to its original length. Then, since the pressure from the piezoelectric element 112 is weakened, the cross section of the tube 120 which forms the liquid chamber 110 is restored from the oval to the circle by a resiliency of the tube 120, and the volume of the liquid chamber 110 is restored to its original volume. Consequently, the liquid supplied from the liquid supply unit 300 flows along the tube 120 and fills the interior of the liquid chamber 110, so that the piezoelectric element 112 shown in FIG. 4A is restored to a state before being driven.

Subsequently, when the piezoelectric element 112 is expanded again due to an increase of the drive voltage, the liquid pressurized in the liquid chamber 110 is ejected from the nozzle 105 as shown in FIG. 5A. By repeating such actions, the pulsation generator 100 in the first embodiment is capable of generating a pulsed jet stream cyclically.

As described above, the pulsation generator 100 is preferably configured in such a manner that the pressure is applied to the side surface of the tube 120 which forms the liquid chamber 110 even in a state in which the drive voltage waveform is not applied to the piezoelectric element 112 and hence the piezoelectric element 112 is not expanded. The reason will be described below.

The piezoelectric element 112 configured of a laminated piezoelectric element has the property of being resistant to a force of compression applied from the outside, but is vulnerable to a force of tension. Then, when the piezoelectric element 112 is compressed, the piezoelectric element 112 is subject to a force in the pulling direction due to the inertia caused by the mass of the element itself. Therefore, the piezoelectric element 112 may have damage such as interlayer peeling or the like. Therefore, with such a configuration in which the pressure is applied to the side surface of the liquid chamber 110 formed of the tube 120 even when the piezoelectric element 112 is contracted, a force in the direction of compression caused by the restoration force of the tube 120 is constantly applied to the piezoelectric element 112. This causes a reduction in the pulling force applied to the piezoelectric element 112. Consequently, occurrence of damage of the piezoelectric element 112 due to the action of the force of tension can be reduced.

According to the first embodiment described above, by forming the spiral-shaped liquid chamber 110 having a substantially constant cross section area between the inflow channel 106a and the outflow channel 106b, the flow of the liquid in the liquid chamber 110 is restricted to a substantially constant velocity along the spiral flow channel. Therefore, accumulation of air bubbles in a portion where the flow of liquid is slow is inhibited, and hence the air bubbles in the liquid chamber can be discharged easily from the outflow channel 106b. Consequently, the pressure in the liquid chamber 110 can be increased sufficiently without being affected by the air bubbles and hence stable ejection of liquid can be maintained.

Also, by keeping the liquid chamber 110 to be pressed by the piezoelectric element 112 also in a state in which the piezoelectric element 112 is not expanded, the force in the direction of compression can be kept from acting on the piezoelectric element 112 in advance as a reaction force of the pressure applied to the liquid chamber 110. Accordingly, when a pulling force is applied to the piezoelectric element 112, the pulling force is alleviated, and hence the probability of damage of the piezoelectric element 112 due to the action of tensile force is reduced.

Furthermore, by keeping the liquid chamber 110 to be pressed by the piezoelectric element 112 also in a state in which the piezoelectric element 112 is not expanded, the volume of the liquid chamber 110 is immediately reduced when the piezoelectric element 112 starts to expand. Therefore, the liquid ejection is efficiently performed without causing any stroke loss between the expansion of the piezoelectric element 112 and the reduction in volume of the liquid chamber 110.

Also, by setting the cross-sectional area of the inflow channel 106a to be smaller than the cross-sectional area of the outflow channel 106b, the pressure in the liquid chamber 110 can be increased while inhibiting a backflow of the liquid to the inflow channel 106a, whereby an outflow from the outlet port 110b having a large cross-sectional area can be facilitated. In this configuration, the backflow can be inhibited even when a check valve or the like is not provided in the inflow channel 106a.

In addition, the ejecting unit 102 and the volume changing unit 101 are configured to be detachable with respect to each other. The ejecting unit 102 is a unit which cause liquid such as water, salt water, or medical solution to flow, and may come into contact with blood or body fluid when the liquid ejecting apparatus 10 is used as a surgical operation tool. Therefore, by configuring the ejecting unit 102 to be capable of being removed from the volume changing unit 101 as a disposable unit, higher security is ensured.

The volume changing unit 101 which does not come into contact with the liquid can be used repeatedly. Since the volume changing unit 101 is costly in comparison with the ejecting unit 102, the running cost can be reduced by using the volume changing unit 101 repeatedly.

The liquid chamber 110 includes a spiral flow channel formed of the flexible tube 120 wound into a spiral shape. In the configuration in which the liquid chamber 110 is formed of the tube 120 in this manner, the layout of the inflow channel 106a and the outflow channel 106b or the wound shape of the tube 120 is not limited by the production method or the like. Therefore, flexibility in design of the liquid chamber 110 is increased, and hence simplification of the structure of the liquid ejecting apparatus 10 or miniaturization of the same is achieved.

Also, by using the tube 120 as the liquid chamber 110, the cross-sectional area of the spiral flow channel can be easily kept substantially constant.

The tube 120 is provided with a gap between each of adjacent turns of the flow channel. The tube 120 is deformed by being pressed by the piezoelectric element 112. In this case, by the provision of the gap between each of the adjacent turns of the flow channel, any increase in load by pressing the adjacent turns of the tube 120 to each other is eliminated, and the pressing amount required for ejecting liquid can be ensured.

Also, the inlet port 110a is arranged at the outer-peripheral-side end of the tube 120 wound in the spiral shape, and the outlet port 110b is arranged at the center-side end of the tube 120 wound into a spiral shape. In the liquid ejecting apparatus 10 configured in this manner, the pressing force in the vicinity of the center of the liquid chamber 110 tends to be stronger than the pressing force in the outer peripheral portion. Therefore, since the pressure is increased as it goes toward the outlet port 110b, the liquid can be pushed out strongly.

The inflow channel 106a which is communicated with the inlet port 110a is arranged on the outer-peripheral-side end of the liquid chamber 110, and the outflow channel 106b which is communicated with the outlet port 110b is arranged at the center-side end. Therefore, when operating the liquid ejecting apparatus 10 while holding with the hand, the nozzle 105 located on an extension of the outflow channel 106b can be arranged at a substantially center of the liquid ejecting apparatus 10, for ease of operability.

Second Embodiment

Subsequently, a second embodiment will be described with reference to the drawings. In the first embodiment described above, the inlet port 110a is arranged on the outer-peripheral-side end of the tube 120, and the outlet port 110b is arranged at the center-side end of the tube 120. In contrast, in the second embodiment, the arrangement of the inlet port 110a and the outlet port 110b is reversed. Therefore, the same functional elements as those in the first embodiment are denoted by the same reference numerals and configurations different from the first embodiment are mainly described.

Figure 6:
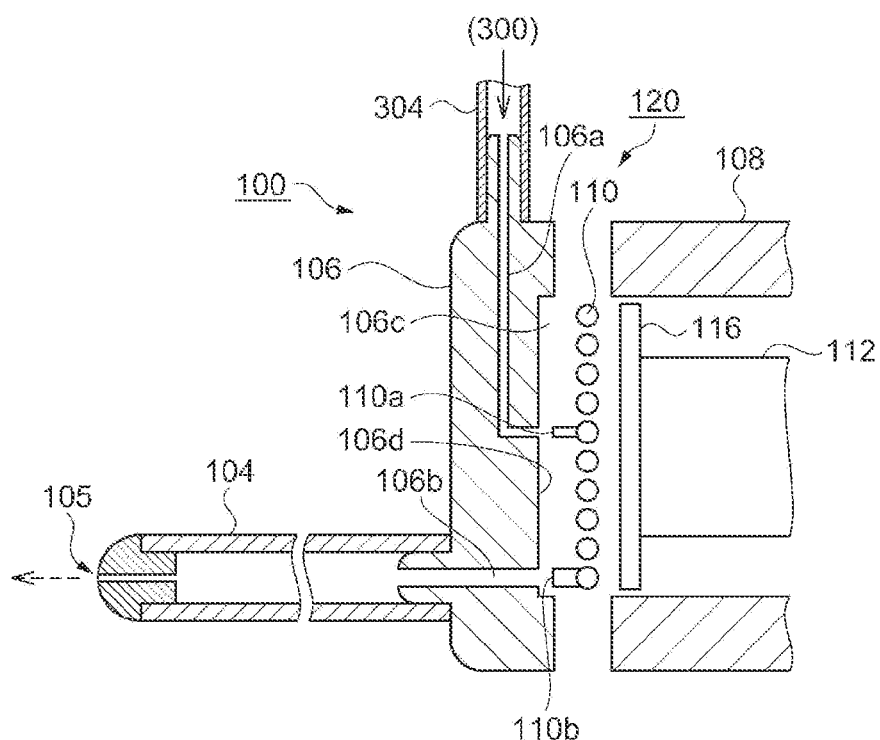
FIG. 6 is an exploded view showing an assembly of part of a pulsation generator according to a second embodiment.

FIG. 6 is an exploded view showing part of an assembly of the pulsation generator 100 according to the second embodiment. The configurations of the first case 108, the piezoelectric element 112, and the reinforcing plate 116 in the second embodiment are the same as those in the first embodiment.

In contrast, the inflow channel 106a which communicates with the second connecting tube 304 connected to the second case 106 is opened at the center position of the depression 106c of the second case 106, and the inlet port 110a of the liquid chamber 110 is connected thereto. Formed at a peripheral edge of the depression 106c is the outflow channel 106b which communicates with the liquid ejecting tube 104, and the outlet port 110b is connected thereto.

The liquid chamber 110 formed of a tube 120 having a circular cross section is arranged in the depression 106c. In the second embodiment, since the configurations of the liquid ejecting tube 104 and the nozzle 105 are the same as those in the first embodiment although the layout is different, detailed description is omitted.

Subsequently, the configuration of the liquid chamber 110 according to the second embodiment will be described.

Figure 7:
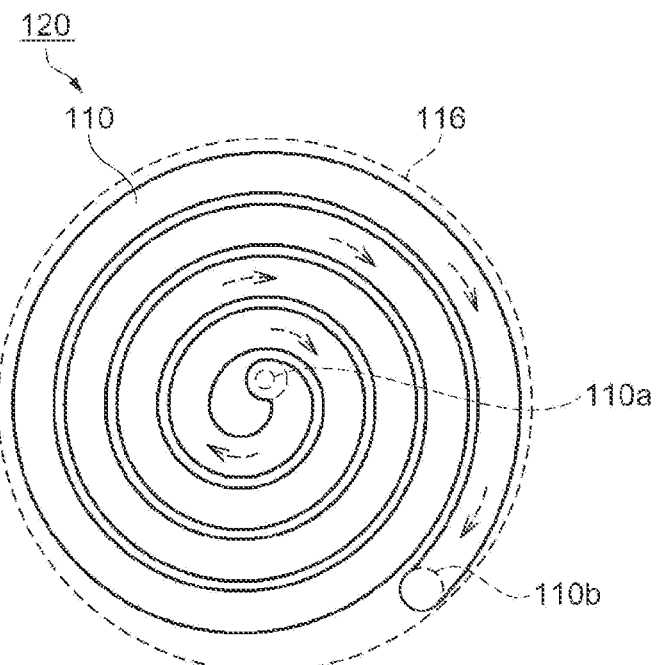
FIG. 7 is an explanatory drawing showing a configuration of a liquid chamber according to the second embodiment.

FIG. 7 is an explanatory drawing showing the configuration of the liquid chamber 110 according to the second embodiment. In FIG. 7, a state of the liquid chamber 110 viewed from the side of the first case 108 is shown. As illustrated, the liquid chamber 110 is formed into a substantially circular shape by winding the tube 120 into a spiral shape. A predetermined gap is formed between each of adjacent turns of the spiral tube 120.

The diameter of the outermost periphery of the spiral shaped tube 120 is set to be smaller than the outer diameter of the circular reinforcing plate 116. Furthermore, an outer-peripheral-side end and a center-side end of the tube 120 are bent toward the second case 106 (see FIG. 6). The inlet port 110a at the center-side end of the spiral-shaped tube 120 which forms the liquid chamber 110 is connected to the inflow channel 106a, and the outlet port 110b at the outer-peripheral-side end is connected to the outflow channel 106b.

The liquid chamber 110 configured in this manner by the tube 120 is installed in the depression 106c of the second case 106. Then, as show in FIG. 6, when mating and securing the second case 106 and the first case 108 with screw cramping, the surface of the tube 120 on one side comes into contact with a depression bottom 106d of the second case 106, and the surface of the tube 120 on the other side comes into contact with the reinforcing plate 116, so that the tube 120 is brought into a state of being sandwiched between the depression bottom 106d and the reinforcing plate 116.

FIG. 7 is a plan view of the liquid chamber 110 according to the second embodiment. The illustrated state is a state in which liquid to be supplied from the liquid supply unit 300 via the second connecting tube 304 to the pulsation generator 100 passes through the inflow channel 106a and flows into the liquid chamber 110, and the liquid chamber 110 is filled with the liquid. The flow of the liquid is indicated by arrows of a broken line in FIG. 7.

The liquid chamber 110 is formed with a spiral flow channel by the tube 120 wound into a spiral shape. Liquid flowing from the inlet port 110a at the center thereof connected to the inflow channel 106a turns along the tube 120 and is guided to the outlet port 110b at the peripheral edge connected to the outflow channel 106b. Since the cross-sectional area of the spiral flow channel of the tube 120 is substantially constant, the liquid in the liquid chamber 110 can flow at a substantially constant velocity from the inlet port 110a to the outlet port 110b.

As described above, since the liquid is supplied from the liquid supply unit 300 at a constant and stabilized pressure, when the liquid chamber 110 is filled with liquid, the liquid in the liquid chamber 110 is pushed out from the outlet port 110b through the outflow channel 106b toward the liquid ejecting tube 104 even when the piezoelectric element 112 is not driven.

Figure 8:
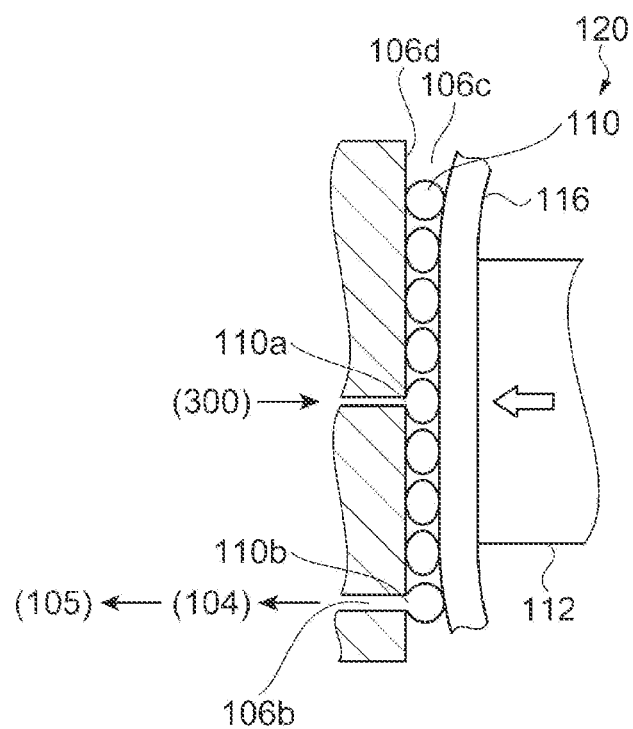
FIG. 8 is a partly cross-sectional view showing a state in which a piezoelectric element according to the second embodiment is driven to press the liquid chamber.

FIG. 8 is a partly cross-sectional view showing a state in which the piezoelectric element 112 is driven to press the liquid chamber 110 according to the second embodiment. In FIG. 8, for easiness of understanding, the deformation of the reinforcing plate 116 is exaggerated.

When the drive voltage waveform is applied to the piezoelectric element 112 in a state in which he liquid chamber 110 is filled with liquid, the piezoelectric element 112 is expanded by an increased drive voltage and presses the tube 120 in the same manner as the first embodiment. The reinforcing plate 116 has the same or larger diameter as the outer diameter of the wound tube 120, and the piezoelectric element 112 is smaller than the outer diameter of the reinforcing plate 116.

When the tube 120, the reinforcing plate 116 and the piezoelectric element 112 are in this relation, if the tube 120 is pressed, the outer peripheral edge of the reinforcing plate 116 is warped about the center portion where the inlet port 110a is disposed as shown in FIG. 8. Therefore, the pressing amount against the liquid chamber 110 is large near the center portion, and hence the change in volume is large in this area. In contrast, the pressing amount is small in the outer peripheral portion, and hence the change in volume of the liquid chamber 110 is small in this area. In other words, the pressure in the liquid chamber 110 seems to be higher in the center portion and be decreased as it goes toward the outer peripheral portion. Therefore, the liquid in the liquid chamber 110 is pushed strongly from the center portion toward the outer peripheral portion.

In this manner, the pressure in the vicinity of the inlet port 110a at the center portion is increased, and the returned pressure of the liquid in the vicinity of the inlet port 110a is increased correspondingly. However, since the inlet port 110a has a capillary shape having a diameter on the order of 0.3 mm, a backflow from the liquid chamber 110 to the inlet port 110a is inhibited. Therefore, the pressure in the liquid chamber 110 can be increased, and hence a strong liquid ejection is achieved.

The spiral flow channel of the liquid chamber 110 is formed by winding the tube 120 in a spiral shape, and the liquid pressurized in the liquid chamber 110 moves to the outlet port 110b at the outer-peripheral-side end along the spiral-shaped tube 120. At this time, the flow rate is increased as the liquid approaches the outlet port 110b and, at a portion close to the outlet port 110b, an amount of the liquid corresponding to the amount of reduction of volume of the liquid chamber 110 moves abruptly and is pushed out from the outlet port 110b. Consequently, the liquid is ejected at a high velocity from the nozzle 105 via the outflow channel 106b and the liquid ejecting tube 104.

When the drive voltage is lowered subsequently, the piezoelectric element 112 contracts and is restored to its original length. Then, since the pressing force applied by the piezoelectric element 112 is weakened, the cross section of the tube 120 which forms the liquid chamber 110 is returned from the oval to the circle by a restoration force of the tube 120, and the volume of the liquid chamber 110 is restored to its original volume. Subsequently, when the piezoelectric element 112 is expanded again due to an increase of the drive voltage, the liquid pressurized in the liquid chamber 110 is ejected from the nozzle 105. By repeating such actions, the pulsation generator 100 in the second embodiment is also capable of generating a pulsed jet stream cyclically.

In the configuration according to the second embodiment, when the tube 120 is pressed by the piezoelectric element 112, the pressing amount at the center portion tends to be larger than the pressing amount of the center portion tends to be larger than the pressing amount of the outer peripheral portion. Therefore, by arranging the inlet port 110a at the center portion, the pressure in the vicinity of the inlet port is increased. In this case, by employing a capillary shape having cross-sectional areas on the order of 0.3 mm (which is smaller than that of the outlet port 110b and the outflow channel 106b) for the inlet port 110a and the inflow channel 106a, a backflow from the liquid chamber 110 to the inlet port 110a is inhibited. Therefore, the pressure in the liquid chamber 110 can be increased, and hence a strong liquid ejection is achieved.

In addition, as described above, since the liquid is pumped from the center portion of the liquid chamber 110 to the outflow channel 106b at the outer-peripheral-side end, movement of the air bubbles is facilitated, further eliminating air bubbles.

Modification

In the first embodiment and the second embodiment described thus far, the liquid chamber 110 is formed into a substantially circular shape by the tube 120 wound into the spiral shape. However, the shape of the liquid chamber 110 formed by the tube 120 is not limited thereto as long as the entire tube 120 can be pressed by the elongation of the piezoelectric element 112. A modification in which the liquid chamber 110 having a shape different from those in the embodiments described above is employed will be described below. In the description of the modification, the same components as in the first embodiment described above are denoted by the same reference numerals in the first embodiment described above, and detailed description will be omitted.

Figure 9:
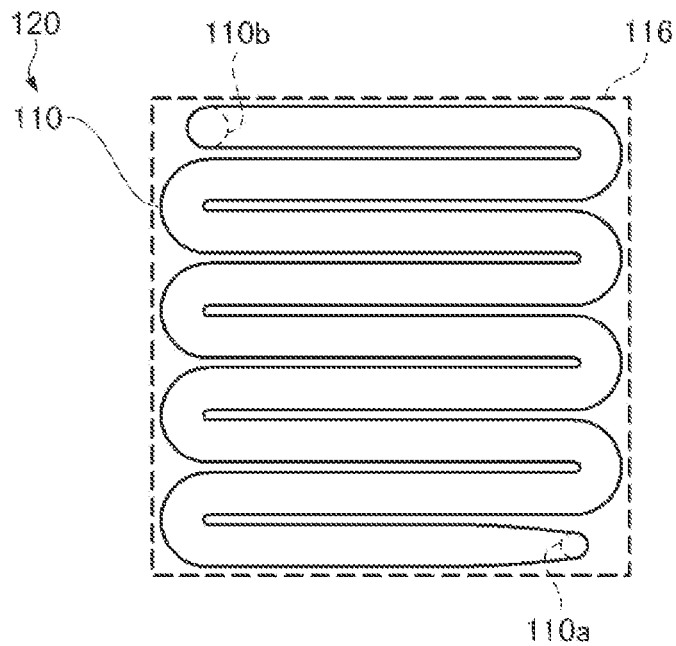
FIG. 9 is an explanatory drawing showing a shape of a liquid chamber according to a modification.

FIG. 9 is an explanatory drawing showing the shape of the liquid chamber 110 according to a modification. As illustrated, the liquid chamber 110 in the modification is formed into a substantially square shape by the tube 120 having a circular cross-section with a uniform cross-sectional area folded in a continuous zigzag pattern. The tube 120 is not clogged at folded portions, and is folded while maintaining its cross-sectional area. The inlet port 110a and the outlet port 110b which form both ends of the tube 120 folded into the square shape are positioned at opposing corners of the square, respectively.

The reinforcing plate 116 is formed into a square shape corresponding to the shape of the liquid chamber 110 as described above, and the size of the reinforcing plate 116 is set to be larger than the outer edge of the tube 120 folded into the square shape, so that the entirety of the liquid chamber 110 can be pressed. Although not illustrated, the second case 106 in the modification is formed with a square shallow depression 106c on the mating surface with respect to the first case 108, and the inflow channel 106a is opened at a corner of the depression 106c, and the outflow channel 106b is formed at an opposed corner.

In the liquid ejecting apparatus 10 in the modification as described above, in the same manner as the embodiments described above, when the piezoelectric element 112 is elongated, the side surface of the tube 120 which forms the liquid chamber 110 is pressed via the reinforcing plate 116. At this time, the cross-sectional shape of the tube 120 is deformed, and hence the volume of the liquid chamber 110 is reduced. Consequently, the liquid pressurized in the liquid chamber 110 can be ejected from the nozzle 105 in a pulsed manner. The liquid flowed from the inlet port 110a to the liquid chamber 110 flows along the folded tube 120 to the outlet port 110b, so that the flow of liquid in the liquid chamber 110 is restricted to a uniform flow. Therefore, accumulation of air bubbles at a portion in which the flow of liquid is slow is avoided, and the air bubbles in the liquid chamber 110 can be discharged quickly.

As is clear from the description above, the shape of the tube 120 which forms the liquid chamber 110 is not limited as long as it can be pressed by the elongation of the piezoelectric element 112, and the arrangement of the inlet port 110a and the outlet port 110b can also be set so as to be aligned with the inflow channel 106a and the outflow channel 106b provided in the second case 106. In this manner, since the flexibility of arrangement of the inlet port 110a and the outlet port 110b, and hence of the inflow channel 106a and the outflow channel 106b is increased, and hence simplification of the structure of the pulsation generator 100 or miniaturization of the same is achieved.

Although the liquid ejecting apparatus 10 in the invention has been described in conjunction with the first embodiment, the second embodiment, and the modification, the invention is not limited to these embodiments and may be implemented in various modes without departing the range of the gist of the invention.

For example, it is also possible to form portions where the tube 120 is turned and portions where the tube 120 is bent between the inlet port 110a and the outlet port 110b by combining the above-described first embodiment or the second embodiment with the modification. In this case as well, the similar effect as the embodiments and the modification described above may be obtained.

In the first embodiment, the second embodiment and the modification described above, the inlet port 110a and the outlet port 110b of the liquid chamber 110 formed of the tube 120 are connected to the inflow channel 106a and the outflow channel 106b formed in the depression 106c of the second case 106 respectively. However, the end portion on the side of the inlet port 110a of the liquid chamber 110 may be formed integrally of the inflow channel 106a and the tube 120.

It is also possible to extend the end portion of the tube 120 on the side of the outlet port 110b to form the outflow channel 106b and the liquid ejecting tube 104 integrally, and then reduce the distal end of the liquid ejecting tube 104 to form the nozzle 105. In this configuration, since the portion from the inflow channel 106a to the nozzle 105 can be formed integrally with the tube 120, leakage of the liquid is prevented at the pulsation generator 100. In this configuration, the tube 120 is preferably formed of a metal.

Third Embodiment

Subsequently, a third embodiment will be described with reference to the drawings. While the liquid chamber 110 is formed of the tube 120 wound into a spiral shape in the first embodiment and the second embodiment, the third embodiment is characterized in that the liquid chamber 110 is formed of a flow channel forming member 130 having a partitioning wall 130w. Common portions to the first embodiment are denoted by the same reference numerals as the first embodiment.

Figure 10:
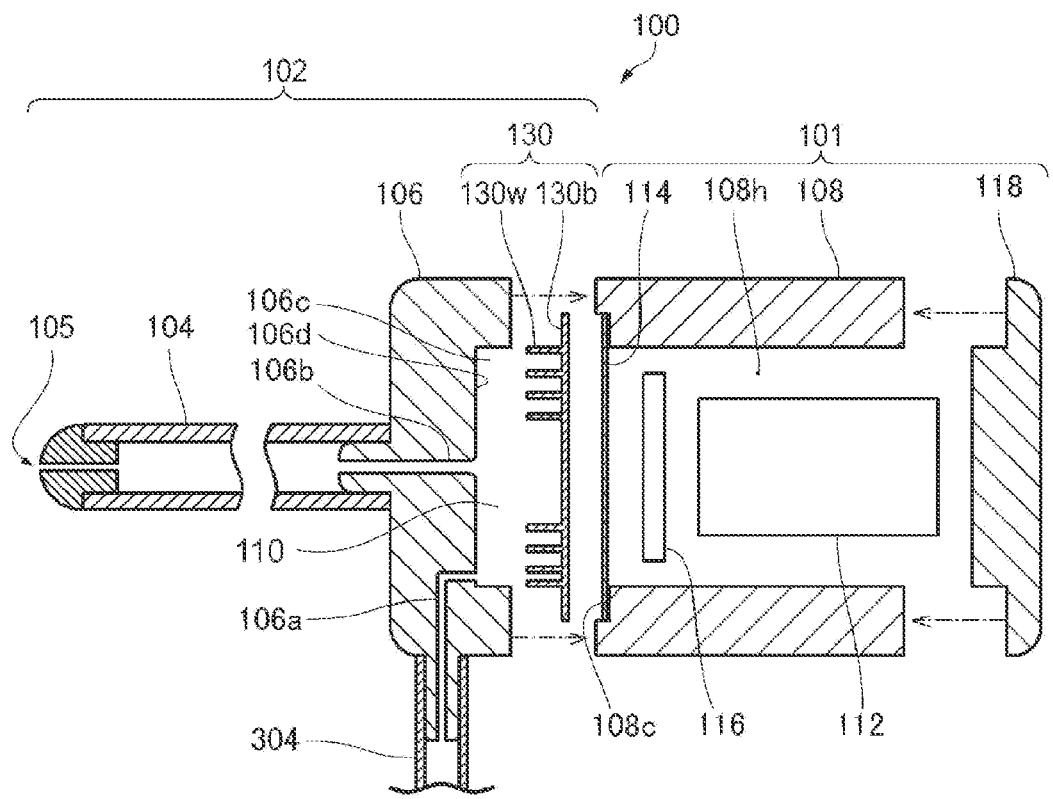
FIG. 10 is an exploded view showing an assembly of a pulsation generator according to a third embodiment.
Figure 11:
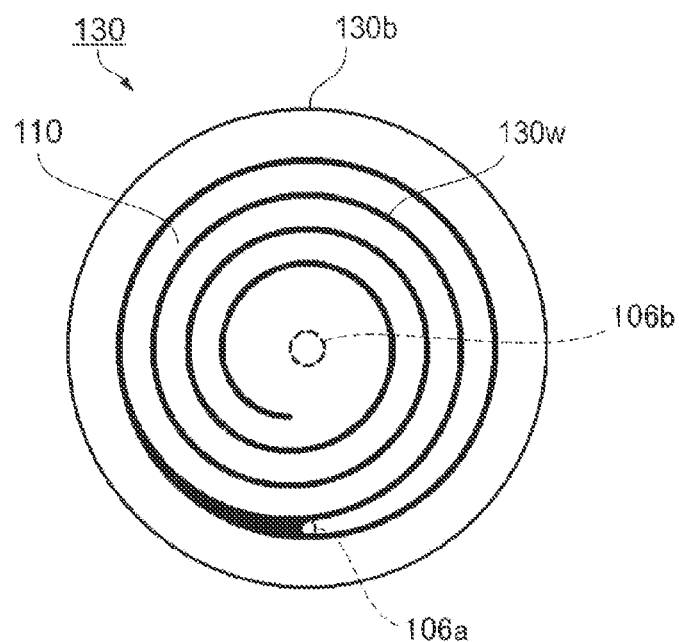
FIG. 11 is a plan view showing the shape of a flow channel forming member according to the third embodiment.

FIG. 10 is an exploded view showing an assembly of the pulsation generator 100 according to the third embodiment. FIG. 11 is a plan view showing the shape of the flow channel forming member 130. The first case 108 is formed with a circular shallow depression 108c at a substantially center position of a mating surface with respect to the second case 106 and the depression 108c is formed with a through hole 108h having a circular cross-section and penetrating through the first case 108. Then, a circular diaphragm 114 formed of a sheet metal or the like is secured to the bottom surface of the depression 108c so as to close the through hole 108h.

The piezoelectric element 112 is accommodated in the through hole 108h closed by the diaphragm 114 and, in addition, the opening of the through hole 108h is closed by the third case 118. Inserted between the piezoelectric element 112 and the diaphragm 114 is the circular reinforcing plate 116. Then, the thickness of the reinforcing plate 116 is set so that the diaphragm 114 and the reinforcing plate 116, the reinforcing plate 116 and the piezoelectric element 112, and the piezoelectric element 112 and the third case 118 barely come into contact with each other in a state in which the piezoelectric element 112 is accommodated in the through hole 108h of the first case 108 and the through hole 108h is closed by the third case 118. An end of the piezoelectric element 112 is secured to the third case 118, and the other end of the piezoelectric element 112 is secured to the reinforcing plate 116. A surface of the reinforcing plate 116 opposite from the piezoelectric element 112 is secured to the diaphragm 114.

On the surface of the diaphragm 114 opposing the second case 106, the flow channel forming member 130 is fitted into the depression 108c so as to mate a supporting panel 130b with the diaphragm 114. The flow channel forming member 130 includes a partitioning wall 130w on one side of the supporting panel 130b so as to extend upright at the side of the first direction toward the second case 106. The supporting panel 130b is secured to the diaphragm 114 on a surface opposite from the surface where the partitioning wall 130w is provided so as to extend upright therefrom. The total thickness of the supporting panel 130b and the diaphragm 114 is determined to be the same as the depth of the depression 108c. Also, the flow channel forming member 130 is formed of a flexible material so as to be deformable. The shape of the partitioning wall 130w of the flow channel forming member 130 will be described later with reference to FIG. 11.

In contrast, the second case 106 is formed with a circular shallow depression 106c on the surface mating the first case 108. The depression 106c is formed to have an inner diameter smaller than the outer diameter of the supporting panel 130b of the flow channel forming member 130 fitted to the first case 108, and to be large enough to receive the partitioning wall 130w extending upright from the supporting panel 130b. The depth of the depression 106c is set to be substantially the same as the height of the partitioning wall 130w.

When the second case 106 and the first case 108 are mated and fixed to each other by screw clamping, the liquid chamber 110 is defined by the depression 106c of the second case 106 and the supporting panel 130b of the flow channel forming member 130 fitted to the side of the first case 108. In addition, the end of the partitioning wall 130w of the flow channel forming member 130 on the side of a first direction opposing the second case 106 is secured to the depression bottom 106d of the depression 106c, and hence a spiral-shaped flow channel (partitioned by the partitioning wall 130w) is formed in the interior of the liquid chamber 110.

In contrast, however, a configuration in which an end of the partitioning wall 130w of the flow channel (forming member 130 on the side of a second direction opposing the first case 108 is secured to the diaphragm 114 provided in the first case 108 in a state in which the supporting panel 130b of the flow channel forming member 130) is secured to the depression bottom 106d of the second case 106 and the second case 106 and the first case 108 are mated and secured to each other by screw clamping is also applicable.

The second case 106 is formed with the inflow channel 106a configured to guide liquid supplied from the second connecting tube 304 connected to the second case 106 to the liquid chamber 110, and the outflow channel 106b configured to guide the liquid pressurized in the liquid chamber 110 to the liquid ejecting tube 104. The inflow channel 106a is opened at a position of the peripheral edge of the depression 106c, and the outflow channel 106b is opened at the center position of the depression 106c.

The liquid ejecting tube 104 is connected to the front surface of the second case 106, and is set to have an inner diameter larger than the inner diameter of the outflow channel 106b. Also, the nozzle 105 (having a liquid ejecting opening set to have an inner diameter smaller than that of the outflow channel 106b) is fitted by insertion to the distal end of the liquid ejecting tube 104. Therefore, the cross-sectional area of a flow channel for allowing passage of liquid flowed from the liquid chamber 110 is increased in the liquid ejecting tube 104 after the outflow channel 106b and then narrowed again at the nozzle 105 at the distal end of the liquid ejecting tube 104.

It is also possible to set the inner diameter of the outflow channel 106b to be the same as the inner diameter of the liquid ejecting tube 104 and connect the outlet port 110b directly to the liquid chamber 110.

Here, a configuration including the first case 108, the third case 118, the piezoelectric element 112, the reinforcing plate 116, and the diaphragm 114 secured to each other is referred to as the volume changing unit 101. A configuration including the second case 106, the liquid ejecting tube 104 (including the nozzle 105), and flow channel forming member 130 are secured to each other or fixed by insertion is referred to as the ejecting unit 102.

The volume changing unit 101 and the ejecting unit 102 are configured to be demountably mountable by screw fixation or the like on the mating surface between the first case 108 and the second case 106.

Referring now to FIG. 11, the configuration of the flow channel forming member 130 will be described. FIG. 11 shows a state of the flow channel forming member 130 viewed from the side of the first case 108 opposing the second case 106. The supporting panel 130b of the flow channel forming member 130 is formed into the same circular shape as the diaphragm 114, and is formed with the spiral-shaped partitioning wall 130w turning inward toward the center portion of the supporting panel 130b on a surface opposing the second case 106 so as to extend upright therefrom.

The spiral-shaped partitioning wall 130w is formed so that the peripheral surface of the outermost turn thereof comes into contact with the inner peripheral surface of the depression 106c and the radial intervals of the wound partitioning wall 130w are set to be substantially constant in the radial direction. As described above, when the second case 106 and the first case 108 are mated and fixed to each other by screw clamping, the spiral-shaped flow channel (directed toward the center while turning inward from the peripheral edge portion) is formed by the partitioning wall 130w in the interior of the liquid chamber 110.

The inflow channel 106a and the outflow channel 106b are connected to the depression 106c of the second case 106. Therefore, when the second case 106 and the first case 108 are mated and secured to each other by screw cramping at an adequate position, the outflow channel 106b opens at the center portion of the spiral flow channel formed in the interior of the liquid chamber 110, and the inflow channel 106a opens at an end portion on the side of the peripheral edge of the spiral flow channel.

With the pulsation generator 100 configured as described above, pulsated ejection of the liquid from the nozzle 105 is achieved by applying the drive voltage waveform on the piezoelectric element 112 to cause expansion and contraction of the piezoelectric element 112. Subsequently, an action of the pulsation generator 100 ejecting the liquid will be described.

Figure 12A:
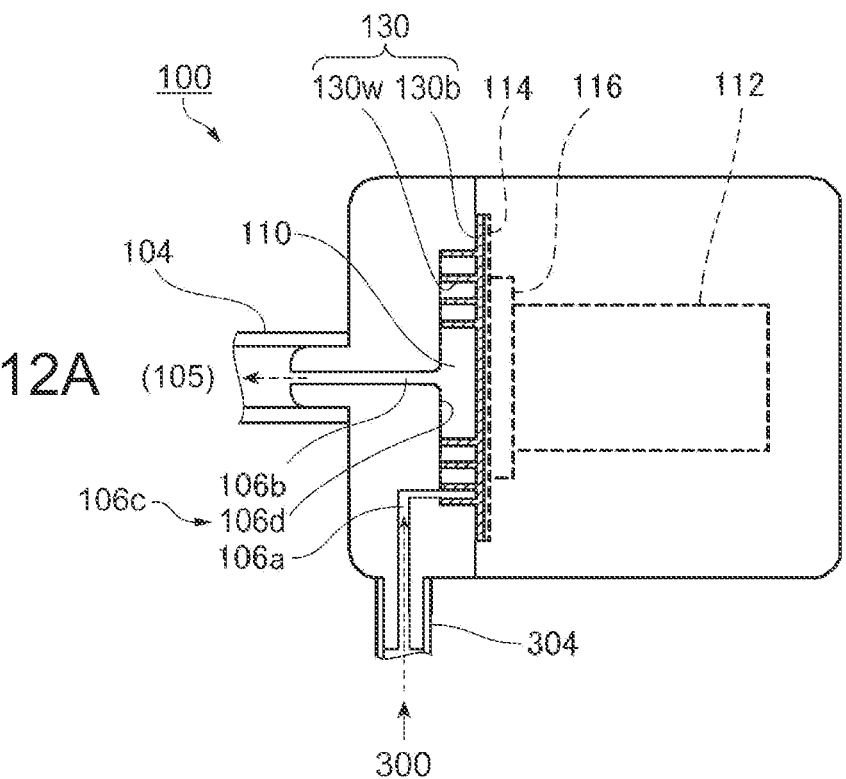
FIG. 12A is a partly cross-sectional view showing a state in which a drive voltage waveform is not applied to the piezoelectric element according to the third embodiment.
Figure 12B:
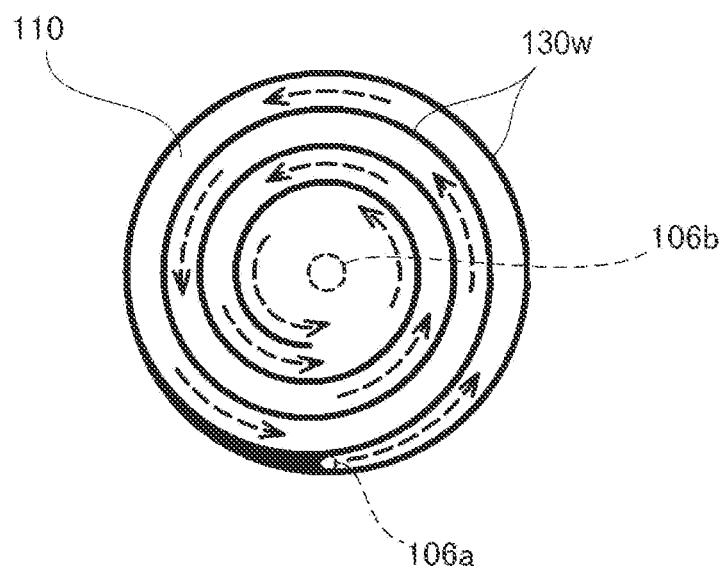
FIG. 12B is a plan view of the liquid chamber in a state in which the drive voltage waveform is not applied to the piezoelectric element according to the third embodiment.
Figure 13A:
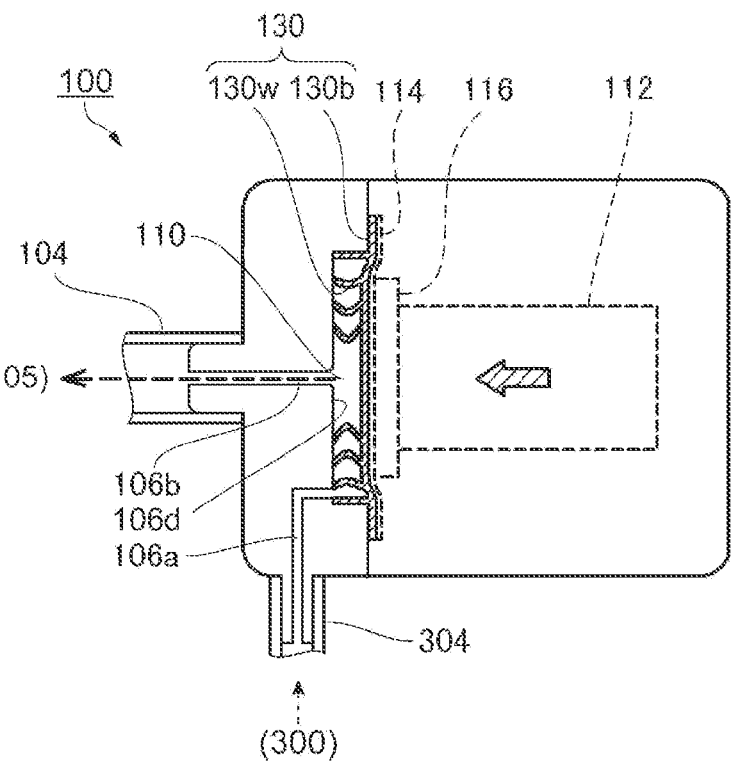
FIG. 13A is a partly cross-sectional view showing a state in which the drive voltage waveform is applied to the piezoelectric element according to the third embodiment.
Figure 13B:
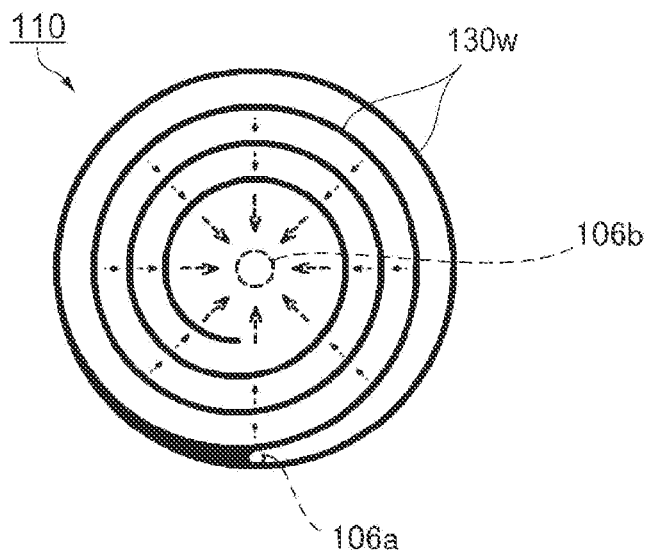
FIG. 13B is a plan view of the liquid chamber in a state in which the drive voltage waveform is applied to the piezoelectric element according to the third embodiment.

FIGS. 12A and 12B and FIGS. 13A and 13B are explanatory drawings schematically showing a liquid ejecting action of pulsation generator 100 in the first embodiment. FIGS. 12A and 12B show a state in which the drive voltage waveform is not applied to the piezoelectric element 112, and FIGS. 13A and 13B show a state in which the drive voltage waveform is applied to the piezoelectric element 112.

Referring now to FIGS. 12A and 12B, the state in which the piezoelectric element 112 is not driven will be described. FIG. 12A is a partly cross-sectional view, and FIG. 12B is a plan view of the liquid chamber 110. In this state, as shown in FIG. 12A, liquid (to be supplied from the liquid supply unit 300 via the second connecting tube 304) passes through the inflow channel 106a and flows into the liquid chamber 110, and the liquid chamber 110 is filled with the liquid. The flow of the liquid is indicated by an arrow of a broken line in FIG. 12A.

The liquid chamber 110 is defined by forming the spiral flow channel partitioning wall 130w into a spiral shape. Liquid flowing from the inflow channel 106a (as indicated by arrows of a broken line shown in FIG. 12B) turns along the partitioning wall 130w and is guided to the outflow channel 106b. Since the cross-sectional area of the spiral flow channel of liquid chamber 110 (defined by the partitioning wall 130w) is substantially constant, the liquid in the liquid chamber 110 can be flowed at a substantially constant velocity from the inflow channel 106a to the outflow channel 106b.

Since the liquid is supplied from the liquid supply unit 300 at a constant stable pressure, when the liquid chamber 110 is filled with liquid, the liquid in the liquid chamber 110 is pushed out through the outflow channel 106b toward the liquid ejecting tube 104 even when the piezoelectric element 112 is not driven.

Referring now to FIGS. 13A and 13B, a state in which the piezoelectric element 112 is driven will be described. FIG. 13A is a partly cross-sectional view, and FIG. 13B is a plan view of the liquid chamber 110. When the drive voltage waveform is applied to the piezoelectric element 112 in a state in which the liquid chamber 110 is filled with liquid, the piezoelectric element 112 is expanded by an increased drive voltage and presses the side surface of the diaphragm 114 and the supporting panel 130b of the flow channel forming member 130 toward the liquid chamber 110 via the reinforcing plate 116 as shown in FIG. 13A. Accordingly, the volume of the liquid chamber 110 is reduced. Consequently, the liquid in the liquid chamber 110 is pressurized. The liquid pressurized in the liquid chamber 110 in this manner is ejected in a pulsed manner from the nozzle 105 via the outflow channel 106b and the liquid ejecting tube 104 as shown by an arrow of a broken line in FIG. 13A.

Two channels, namely, the inflow channel 106a and the outflow channel 106b are communicated with the liquid chamber 110. Therefore, the liquid pressurized in the liquid chamber 110 is considered to flow out not only from the outflow channel 106b, but also from the inflow channel 106a. However, since flowability of the liquid in the flow channel is determined by the cross-sectional area of the flow channel, the length of the flow channel or the like, the liquid is allowed to flow out easier from the outflow channel 106b than from the inflow channel 106a by setting the cross-sectional areas or the lengths of the inflow channel 106a and the outflow channel 106b adequately. For example, in this embodiment, the diameter of the outflow channel 106b is on the order of 1 mm, and the inflow channel 106a has a capillary shape having a diameter on the order of 0.3 mm. Therefore, the backflow from the inflow channel 106a is inhibited.

Since there is a flow of liquid pumped out from the liquid supply unit 300 at the inflow channel 106a which is urged to flow into the liquid chamber 110, outflow of the liquid in the liquid chamber 110 can be prevented. However, there are but few elements which resist the outflow of the liquid in the liquid chamber 110, or which increase the fluid inertia that exists in the outflow channel 106b. Therefore, the liquid pressurized in the liquid chamber 110 exclusively flows out from the outflow channel 106b and is ejected from the nozzle 105 at the distal end thereof via the liquid ejecting tube 104.

The interior of the liquid chamber 110 in the third embodiment is partitioned into a spiral shape by the partitioning wall 130w of the flow channel forming member 130. However, when the volume of the liquid chamber 110 is reduced due to the extension of the piezoelectric element 112, the liquid in the liquid chamber 110 flows not only along the spiral-shaped partitioning wall 130w, but also toward the center of the liquid chamber 110 upon deformation of the partitioning wall 130w toward the outflow channel 106b. This point will be described as a postscript below.

When considering the partitioning wall 130w which constitutes the innermost turn of the multiply wound spiral-shaped partitioning wall 130w as an example, since the outflow channel 106b is opened at the center portion of the liquid chamber 110 inside the innermost turn of the partitioning wall 130w. Therefore, when the volume of the liquid chamber 110 is reduced, the liquid flows out from the outflow channel 106b and hence the pressure rise in the pulsation generator 100 is inhibited.

In contrast, since the inflow channel 106a has a capillary shape and inhibits the outflow of the liquid, the pressure rises more on the outside of the partitioning wall 130w than on the inside of the partitioning wall 130w. Since the partitioning wall 130w is formed of a flexible material so as to be deformable, the liquid pushes the partitioning wall 130w from the outside under the higher pressure toward the inside under the lower pressure and deforms the same to reduce the pressure difference between the inside and the outside. Since the partitioning wall 130w in the third embodiment extends upright from the supporting panel 130b, and is secured at the distal end to the depression bottom 106d of the second case 106, the center portion of the partitioning wall 130w is deformed so as to bend inward by being pushed from the outside as shown in FIG. 13A.

The pressure difference between the inside and the outside of the partitioning wall 130w as described above is generated not only around the innermost turn of the partitioning wall 130w, but also around the second innermost turn of the partitioning wall 130w due to the inward deformation of the innermost turn of the partitioning wall 130w and lowering of the outside pressure. This phenomenon propagates also to the third innermost turn of the partitioning wall 130w in the same manner. Therefore, the spiral-shaped partitioning wall 130w is deformed as a whole toward the center of the liquid chamber 110 so as to contract the spiral flow channel. The displacement of the partitioning wall 130w is the largest on the innermost turn of the partitioning wall 130w having a small inner diameter as shown in FIG. 13A.

In this manner, when the volume of the liquid chamber 110 is reduced due to the elongation of the piezoelectric element 112, the center portion of the spiral-shaped partitioning wall 130w is deformed so as to bend toward the center of the liquid chamber 110, so that the liquid in the liquid chamber 110 is urged toward the outflow channel 106b at the center of the liquid chamber 110 to move in the direction indicated by arrows of a broken line shown in FIG. 13B.

When the volume of the liquid chamber 110 is reduced by the expansion of the piezoelectric element 112, the liquid of an amount corresponding to the reduced volume is collected to the outflow channel 106b and then is pushed out therefrom, so that the liquid is ejected from the nozzle 105 at the distal end of the liquid ejecting tube 104. At this time, it is also considered that a sufficient amount of liquid cannot be collected from the periphery to the outflow channel 106b at the center by being hindered by the spiral-shaped partitioning wall 130w in the liquid chamber 110. However, in the pulsation generator 100 according to the third embodiment, the amount of displacement of the liquid chamber 110 due to the expansion thereof is small, and the amount of liquid ejected by one pulse is on the order of $1/100$ of the volume of the liquid chamber 110. Therefore, a sufficient amount of liquid can be collected to the outflow channel 106b from the periphery by a slight deformation of the partitioning wall 130w toward the center of the liquid chamber 110.

For example, when the ejecting amount V is assumed to be $1/100$ of the volume of the liquid chamber 110, and R is the inner radius of the liquid chamber 110 and H is the thickness of the liquid chamber 110, that is, the depth of the depression 106c, the following expression is established.

$$V = \pi R^2 H/100 \quad (1)$$

When it is assumed that liquid is ejected from the nozzle 105 by an amount collected to and pushed out from the outflow channel 106b by the displacement of the innermost turn of the partitioning wall 130w toward the center of the liquid chamber 110 by a distance s, the injection amount V corresponds to the difference between the volume V1 of the inside of the innermost turn before deformation and the volume V2 of the inside of the innermost turn after the deformation. Therefore, when r is an inner radius of the innermost turn of the spiral-shaped partitioning wall 130w, the following expressions are established.

$$V1 = \pi r^2 H$$
$$V2 = \pi (r-s)^2 H$$
$$V = V1 - V2$$
$$= \pi H\{r^2 - (r^2 - 2rs + s^2)\}$$
$$= \pi H(2rs - s^2)$$

Here, if the distance s is just a slight amount of displacement, $s^2$ is negligible. Therefore, the following approximation is established.

$$V \approx 2\pi rsH \quad (2)$$

Then, when the inner radius r of the innermost turn of partitioning wall 130w is set to a half (½) the inner radius R of the liquid chamber 110 for example, from the expressions (1) and (2), the following equations are established.

$$2\pi(R/2)sH = \pi R^2 H/100 \quad (3)$$

$$s = R/100 \quad (4)$$

Therefore, an amount of liquid corresponding to the ejecting amount can be collected to the outflow channel 106b only by a slight displacement of the innermost turn of the partitioning wall 130w toward the center of the liquid chamber 110 in a scale of $1/100$ of the inner diameter of the liquid chamber 110. Therefore, the spiral-shaped partitioning wall 130w in the liquid chamber 110 does not hinder the liquid ejection.

After having ejected the liquid, the piezoelectric element 112 is contracted to its original length by the reduction of the drive voltage. Accordingly, the volume of the liquid chamber 110 is restored to its original volume. The liquid supplied from the liquid supply unit 300 to the liquid chamber 110 flows along the partitioning wall 130w and hence the interior of the liquid chamber 110 is filled therewith, and the partitioning wall 130w in the liquid chamber 110 is restored to its original upright state. Consequently, the piezoelectric element 112 shown in FIG. 12A is restored to its original state.

When the piezoelectric element 112 is expanded again due to an increase of the drive voltage, the liquid pressurized in the liquid chamber 110 is ejected from the nozzle 105 as shown in FIG. 13A. By repeating such actions, the pulsation generator 100 in the third embodiment is also capable of ejecting the liquid from the nozzle 105 in a pulsed manner.

According to the third embodiment described above, the liquid chamber 110 is partitioned into the spiral-shaped flow channel having a substantially constant cross-sectional area by the deformable partitioning wall 130w between the inflow channel 106a and the outflow channel 106b. Then, when the piezoelectric element 112 is driven in a state in which the liquid supplied from the inflow channel 106a is filled in the liquid chamber 110, the partitioning wall 130w is deformed and hence the volume of the liquid chamber 110 is reduced, the liquid pressurized in the liquid chamber 110 flows along the spiral-shaped flow channel and is guided to the outflow channel 106b, and the liquid is ejected from the nozzle 105 through the outflow channel 106b. Therefore, since the liquid flows at a sufficiently high flow velocity along the spiral flow channel, accumulation of air bubbles at a portion in which the flow of liquid is slow is inhibited, so that the air bubbles in the liquid chamber 110 can be discharged quickly from the outflow channel 106b. Consequently, the pressure in the liquid chamber 110 can be increased sufficiently without being affected by the air bubbles and hence stable ejection of liquid can be performed.

The partitioning wall 130w which defines the spiral flow channel in the interior of the liquid chamber 110 is formed of a flexible material and hence is deformable, when the volume of the liquid chamber 110 is reduced by the expansion of the piezoelectric element 112, the center portion of the spiral-shaped partitioning wall 130w is deformed so as to be bent toward the center of the liquid chamber 110. Accordingly, the pressurized liquid in the liquid chamber 110 can move toward the center of the liquid chamber 110. Therefore, a flow of the liquid directed toward the outflow channel 106b opened at the center is generated inside the innermost turn of the spiral-shaped partitioning wall 130w, and hence the liquid is collected to the outflow channel 106b from the periphery. In this manner, in the liquid ejecting apparatus 10 in this embodiment, even though the partitioning wall 130w is provided inside the liquid chamber 110, ejection of the liquid is not hindered by the partitioning wall 130w, and hence the liquid can be ejected strongly.

Fourth Embodiment

In addition to the pulsation generator 100 according to the third embodiment described above, an embodiment in which the technical thought in the third embodiment is developed may be realized. Such other embodiments will be described below. In the description of these embodiments, the same components as the third embodiment are denoted by the same reference numerals as the third embodiment, and detailed description of the common portions will be omitted.

Figure 14A:
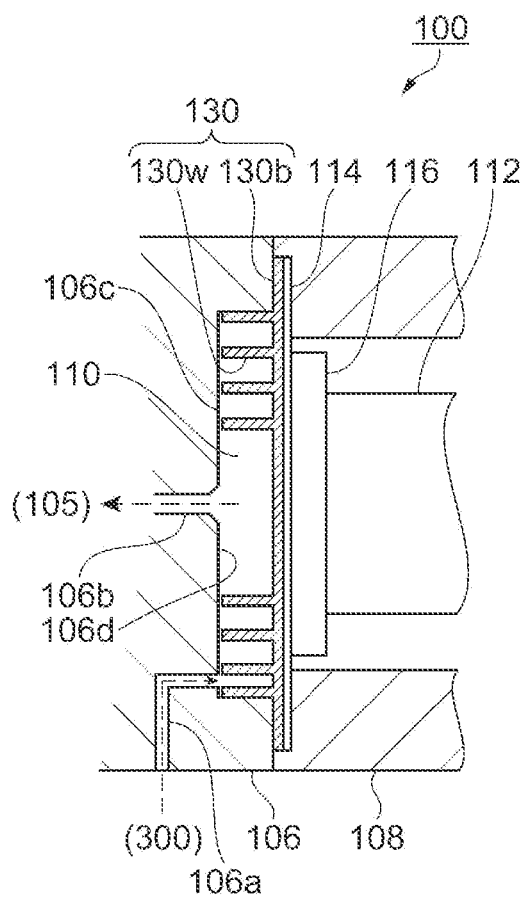
FIG. 14A is a partly cross-sectional view of an internal structure of a pulsation generator according to a fourth embodiment in a state in which a drive voltage waveform is not applied to the piezoelectric element.
Figure 14B:
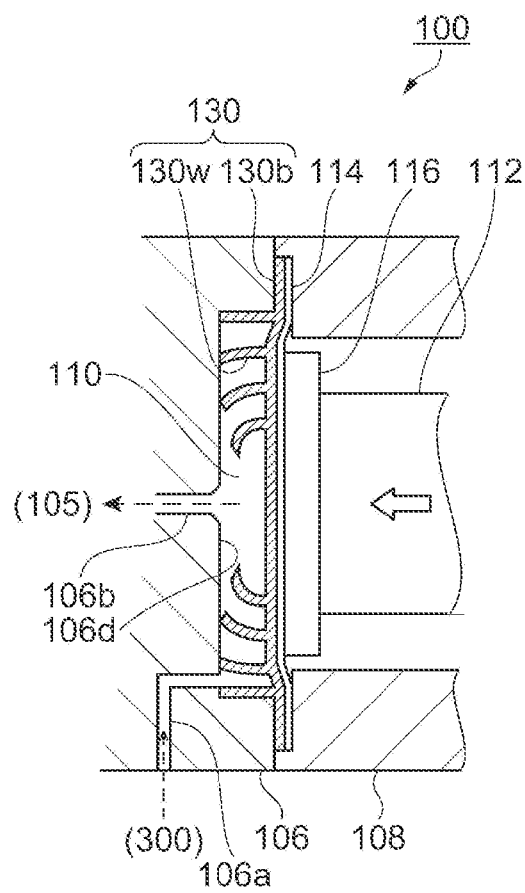
FIG. 14B is a partly cross-sectional view of the internal structure of the pulsation generator according to the fourth embodiment in a state in which the drive voltage waveform is applied to elongate the piezoelectric element.

FIG. 14A is an explanatory drawing of an internal structure of a pulsation generator 100 according to a fourth embodiment in a state in which a drive voltage waveform is not applied to the piezoelectric element 112. FIG. 14B is an explanatory drawing of the internal structure of the pulsation generator 100 according to the fourth embodiment in a state in which the drive voltage waveform is applied to elongate the piezoelectric element 112. In the third embodiment described above, the partitioning wall 130w of the flow channel forming member 130 extends upright from the supporting panel 130b, and the distal end thereof is secured to the depression bottom 106d of the second case 106. However, in the fourth embodiment, the distal end of the partitioning wall 130w is not secured to the depression bottom 106d of the second case 106.

As shown in FIG. 14A, the flow channel forming member 130 is provided with the spiral-shaped partitioning wall 130w so as to extend upright from the supporting panel 130b. Formed in the interior of the liquid chamber 110 is a spiral flow channel partitioned by the partitioning wall 130w. However, in the fourth embodiment, unlike the third embodiment described above, the end portion of the partitioning wall 130w on the side of the first direction opposing the second case 106 is not secured to the depression bottom. 106d of the second case 106, and a small gap is provided between the distal end portion of the partitioning wall 130w and the depression bottom 106d.

In the pulsation generator 100 according to the fourth embodiment as well, in the same manner as the third embodiment, the liquid flowing from the inflow channel 106a opening on the peripheral edge portion of the liquid chamber 110 flows to the outflow channel 106b at the center while turning along the partitioning wall 130w, whereby the liquid chamber 110 is filled with the liquid. Since the gap between the distal end of the partitioning wall 130w and the depression bottom 106d is very small, the liquid flowed into the liquid chamber 110 is exclusively flows along the spiral flow channel.

When the piezoelectric element 112 is expanded by an application of a drive voltage waveform in a state in which the liquid chamber 110 is filled with the liquid in this manner, the volume of the liquid chamber 110 is reduced, and the liquid in the liquid chamber 110 is pressurized. At this time, since a pressure difference is generated between the inside and the outside of the partitioning wall 130w, the partitioning wall 130w is pressed from the outside with a higher pressure to the inside with a lower pressure and hence is deformed. In the pulsation generator 100 according to the fourth embodiment, since the distal end of the partitioning wall 130w is not secured to the depression bottom 106d of the second case 106, the distal end side of the partitioning wall 130w is deformed so as to incline toward the center of the liquid chamber 110 as shown in FIG. 14B.

In this manner, when the distal end side of the partitioning wall 130w is inclined toward the center of the liquid chamber 110, the liquid on the outside of the partitioning wall 130w flows into the inside beyond the partitioning wall 130w. Therefore, a flow of the liquid flowing toward the outflow channel 106b at the center across the spiral flow channel is generated in the interior of the liquid chamber 110.

As described thus far, in the pulsation generator 100 according to the fourth embodiment, the distal end of the partitioning wall 130w is not secured to the depression bottom 106d of the second case 106. However, when the liquid chamber 110 is filled with the liquid, the flow of the liquid in the liquid chamber 110 can be restricted to a constant flow velocity along the spiral flow channel formed by the partitioning wall 130w in the same manner as the third embodiment described above. Therefore, accumulation of air bubbles at a portion in which the flow of liquid is slow is avoided, and the air bubbles in the liquid chamber 110 can be discharged quickly.

Also, when the piezoelectric element 112 is expanded and the volume of the liquid chamber 110 is reduced, the distal end of the partitioning wall 130w which is not secured to the depression bottom 106d of the second case 106 falls toward the center of the liquid chamber 110, whereby the liquid flowing toward the outflow channel 106b at the center beyond the partitioning wall 130w is generated in the interior of the liquid chamber 110. In this manner, since the liquid is collected to the outflow channel 106b at the center from the periphery together with the flow flowing across the spiral flow channel, the liquid can be ejected adequately.

Fifth Embodiment

Subsequently, the pulsation generator 100 according to a fifth embodiment will be described. In the third embodiment and the fourth embodiment, the partitioning wall 130w of the flow channel forming member 130 is provided so as to extend upright from the supporting panel 130b. The fifth embodiment is characterized in that the partitioning wall 130w on the inner peripheral side of the spiral shape is not provided so as to extend upright from the supporting panel 130b.

Figure 15A:
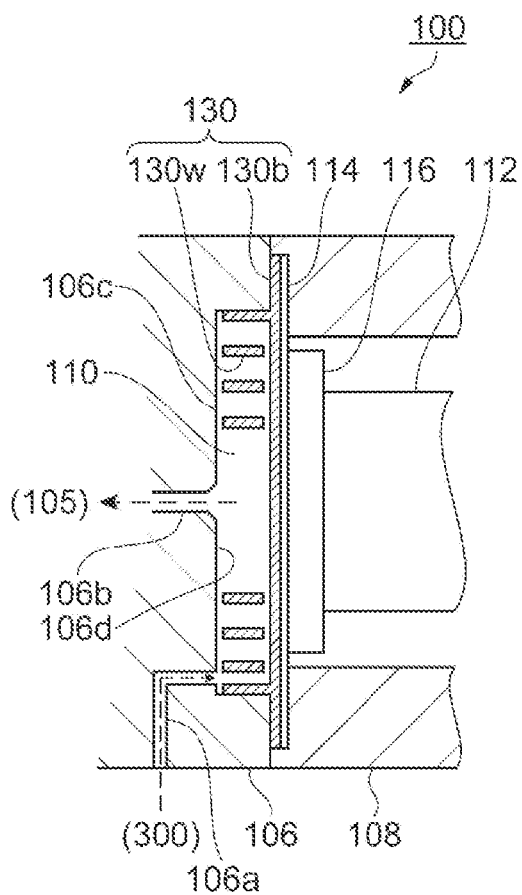
FIG. 15A is a partly cross-sectional view of an internal structure of a pulsation generator according to a fifth embodiment in a state in which a drive voltage waveform is not applied to the piezoelectric element.
Figure 15B:
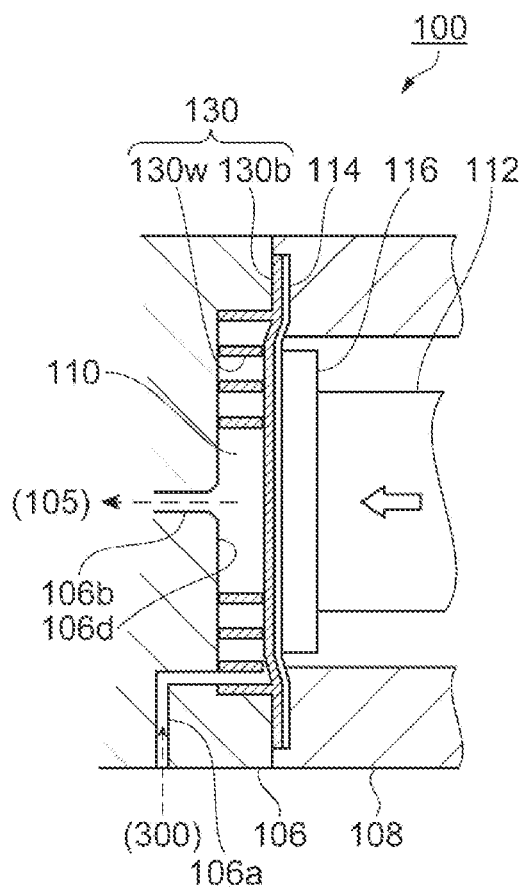
FIG. 15B is a partly cross-sectional view of the internal structure of the pulsation generator according to the fifth embodiment in a state in which the drive voltage waveform is applied to elongate the piezoelectric element.

FIG. 15A is an explanatory drawing showing an internal structure of the pulsation generator 100 according to the fifth embodiment in a state in which a drive voltage waveform is not applied to the piezoelectric element 112. FIG. 15B is an explanatory drawing showing the internal structure of the pulsation generator 100 according to the fifth embodiment in a state in which the drive voltage waveform is applied to the piezoelectric element 112 and hence the piezoelectric element 112 is expanded. In the pulsation generator 100 according to the fifth embodiment, the spiral flow channel divided by the spiral-shaped partitioning wall 130w is formed in the interior of the liquid chamber 110 in the same manner as the third embodiment and the fourth embodiment described above.

The partitioning wall 130w is not secured to the depression bottom 106d of the second case 106, and a small gap is provided with respect to the depression bottom 106d. The partitioning wall 130w does not extend entirely upright from the supporting panel 130b. Only a portion of the multiply wound spiral partitioning wall 130w which constitutes the outermost tern extends upright from the supporting panel 130b, and the remaining portion does not extend upright from the supporting panel 130b and has a small gap therefrom although having a continuous spiral shape.

In the pulsation generator 100 according to the fifth embodiment configured in this manner as well, when the liquid chamber 110 is filled with the liquid, the flow of the liquid in the liquid chamber 110 is restricted to a constant flow velocity along the spiral flow channel formed by the partitioning wall 130w in the same manner as the third and fourth embodiments, the air bubbles in the liquid chamber 110 can be discharged quickly.

In contrast, as shown in FIG. 15B, when the volume of the liquid chamber 110 is reduced by the expansion of the piezoelectric element 112 and hence the pressure difference between the inside and the outside of the partitioning wall 130w occurs, the partitioning wall 130w is pressed from the outside with a higher pressure toward the inside with a lower pressure. At this time, the portion of the spiral-shaped partitioning wall 130w (which is not fixed to the supporting panel 130b) is moved toward the center of the liquid chamber 110 as if a spring is wound up. Therefore, the pressurized liquid in the liquid chamber 110 is moved toward the center of the liquid chamber 110. In addition, a flow of the liquid toward the outflow channel 106b at the center is generated so as to intersect the spiral flow channel beyond the partitioning wall 130w and hence the liquid is collected to the outflow channel 106b from the periphery, so that the liquid can be ejected strongly.

In the above-describe third, fourth and the fifth embodiments, the liquid supplied to the liquid chamber 110 is guided to the outflow channel 106b efficiently. Therefore, when the outflow channel 106b is configured to be opened at the center position of the depression 106c which constitutes the liquid chamber 110. However, the position where the outflow channel 106b is opened is not limited to the center position of the depression 106c as long as at least the positional relationship such that the outflow channel 106b is opened at a position closer to the center of the depression 106c than the inflow channel 106a is ensured.

Sixth Embodiment

Subsequently, the pulsation generator 100 according to a sixth embodiment will be described. In the third, fourth, and fifth embodiments described above, the outflow channel 106b is opened at the center portion of the liquid chamber 110 formed into the spiral shape and the inflow channel 106a is opened at the outer peripheral edge portion of the liquid chamber 110. In contrast, the sixth embodiment is characterized in that the outflow channel 106b is opened at the outer peripheral edge portion of the liquid chamber 110 formed into the spiral shape, and the inflow channel 106a is opened at the center portion of the liquid chamber 110. Therefore, in the description of the sixth embodiment, the same components as the third embodiment are denoted by the same reference numerals as the third embodiment described above, and detailed description of the common portions will be omitted.

Figure 16:
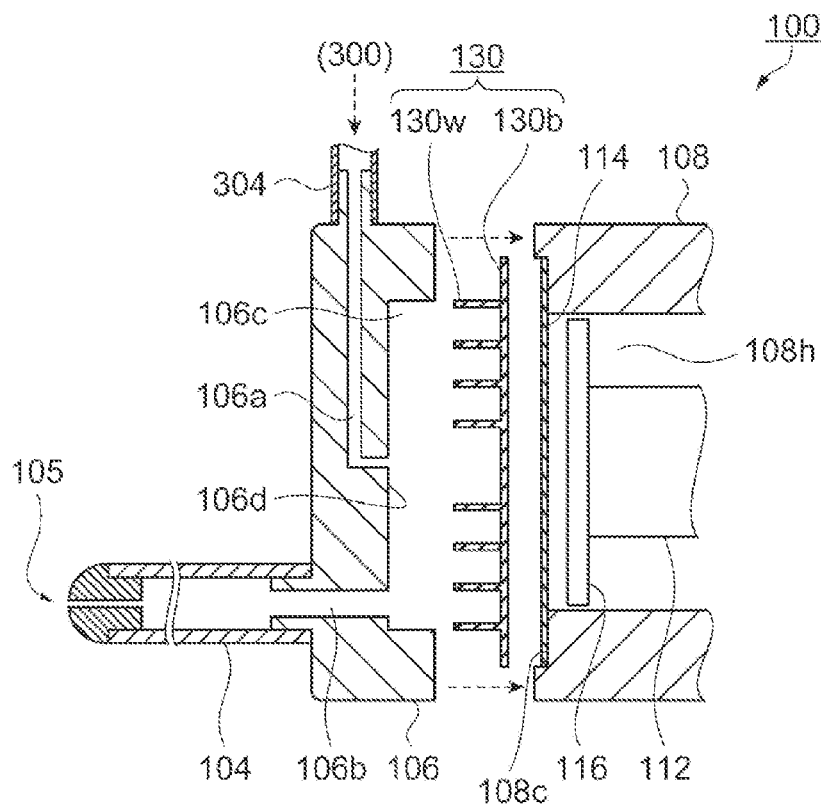
FIG. 16 is an exploded view showing an assembly of a pulsation generator according to a sixth embodiment.

FIG. 16 is an exploded view showing an assembly of the pulsation generator 100 according to a sixth embodiment. The pulsation generator 100 is formed with a circular shallow depression 108c at a substantially center position of a mating surface between the first case 108 and the second case 106. Furthermore, a circular diaphragm 114 formed of a metal sheet or the like is secured to the bottom surface of the depression 108c so as to close the through hole 108h.

The piezoelectric element 112 is accommodated in the through hole 108h closed by the diaphragm 114. Inserted between the piezoelectric element 112 and the diaphragm 114 is the circular reinforcing plate 116. The thickness of the reinforcing plate 116 is set so that the diaphragm 114 and the reinforcing plate 116, and the piezoelectric element 112 and the third case 118 barely come into contact with each other. An end of the piezoelectric element 112 is secured to the third case 118 (not shown), and the other end of the piezoelectric element 112 is secured to the reinforcing plate 116. A surface of the reinforcing plate 116 opposite from the piezoelectric element 112 is secured to the diaphragm 114.

On the side of the diaphragm. 114 opposing the second case 106, the flow channel forming member 130 (having the partitioning wall 130w extending upright from one surface of the circular supporting panel 130b) is fitted into the depression 108c so as to mate a supporting panel 130b with the diaphragm 114. A surface of the supporting panel 130b (opposite from the surface where the partitioning wall 130w extends upright therefrom) is secured to the diaphragm 114. The total thickness of the supporting panel 130b and the diaphragm 114 is set to be the same as the depth of the depression 108c. The flow channel forming member 130 is formed of a flexible material so as to be deformable. The shape of the partitioning wall 130w will be described later with reference to FIG. 17.

In contrast, the second case 106 is formed with a circular shallow depression 106c on the surface mating the first case 108. Then, when the second case 106 and the first case 108 are mated and fixed to each other by screw clamping, the liquid chamber 110 is defined by the depression 106c of the second case 106 and the flow channel forming member 130 provided on the side of the first case 108. In addition, the distal end of the partitioning wall 130w of the flow channel forming member 130 on the side opposing the second case 106 is secured to the depression bottom 106d of the second case 106. Hence a spiral-shaped flow channel partitioned by the partitioning wall 130w is formed in the interior of the liquid chamber 110.

In contrast, however, a configuration is also applicable in which an end of the partitioning wall 130w of the flow channel forming member 130 on the side opposing the diaphragm 114 is secured to the diaphragm 114 in a state in which the supporting panel 130b of the flow channel forming member 130 is secured to the depression bottom 106d of the second case 106 and the second case 106 and the first case 108 are mated and secured to each other by screw cramping.

The inflow channel 106a is communicated with the center portion of the spiral-shaped liquid chamber 110, and the outflow channel 106b is communicated with the outer peripheral edge portion. The second connecting tube 304 is connected to the inflow channel 106a, and the liquid ejecting tube 104 is connected to the outflow channel 106b.

Figure 17:
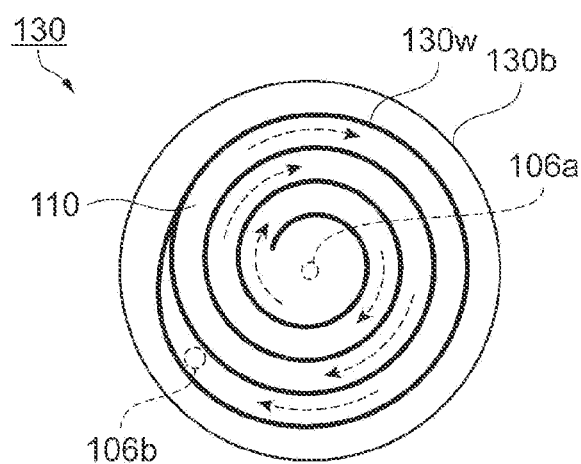
FIG. 17 is an explanatory drawing showing the shape of a flow channel forming member according to the sixth embodiment.

Referring now to FIG. 17, the configuration of the flow channel forming member 130 according to the sixth embodiment will be described.

FIG. 17 is an explanatory drawing showing the shape of the flow channel forming member 130. FIG. 17 shows a state of the flow channel forming member 130 viewed from the diaphragm 114 side. As illustrated, the supporting panel 130b of the flow channel forming member 130 is formed into the same circular shape as the diaphragm 114, and is formed with the spiral-shaped partitioning wall 130w turning inward toward the center portion of the supporting panel 130b on a surface opposing the second case 106 of the supporting panel 130b so as to extend upright therefrom.

The spiral-shaped partitioning wall 130w is formed so that part of the outermost peripheral surface thereof comes into contact with the inner peripheral surface of the depression 106c and the cross-sectional area of the spiral flow channel between the inflow channel 106a and the outflow channel 106b is substantially constant. When the second case 106 and the first case 108 are mated and fixed to each other by screw clamping, the spiral-shaped flow channel directed toward the outer peripheral edge portion while turning inward from the center portion is defined by the partitioning wall 130w in the interior of the liquid chamber 110.

Also, as shown in FIG. 16, the inflow channel 106a and the outflow channel 106b are communicated with the depression 106c of the second case 106. Therefore, when the second case 106 and the first case 108 are mated and secured to each other by screw clamping at an adequate position, the inflow channel 106a opens at an end portion on side of the center of the spiral flow channel formed in the interior of the liquid chamber 110 and the outflow channel 106b opens at an end portion on the side of the outer peripheral edge of the spiral flow channel.

With the pulsation generator 100 configured as described above as well, pulsated ejection of the liquid from the nozzle 105 is achieved by applying the drive voltage waveform on the piezoelectric element 112 to cause expansion and contraction of the piezoelectric element 112.

Subsequently, a liquid ejecting action of the pulsation generator 100 according to a sixth embodiment will be described. In a state in which the piezoelectric element 112 is not driven (in a state in which the drive voltage waveform is not applied), as shown in FIGS. 16 and 17, liquid flows from the liquid supply unit 300 into the liquid chamber 110 via the second connecting tube 304 through the inflow channel 106a, so that the liquid chamber 110 is filled with the liquid.

Formed in the interior of the liquid chamber 110 is a spiral flow channel having a substantially constant cross-sectional area by being partitioned by the partitioning wall 130w of the flow channel forming member 130. The liquid flowed into the liquid chamber 110 from the inflow channel 106a opening at the center portion thereof is guided to the outflow channel 106b opening at the outer peripheral edge portion of the liquid chamber 110 while turning along the partitioning wall 130w as indicated by arrows in a broken line in FIG. 17. In this manner, by restricting the flow of the liquid along the partitioning wall 130w, the variations in flow velocity in the liquid chamber 110 from part to part do not occur in the liquid chamber 110. Consequently, the liquid flowed into the liquid chamber 110 from the inflow channel 106a flows to the outflow channel 106b at substantially constant flow velocity.

Since the liquid is supplied from the liquid supply unit 300 at a substantially constant pressure without any interruption, when the liquid chamber 110 is filled with liquid, the liquid in the liquid chamber 110 is pushed out through the outflow channel 106b toward the liquid ejecting tube 104 even when the piezoelectric element 112 is not driven.

Figure 18A:
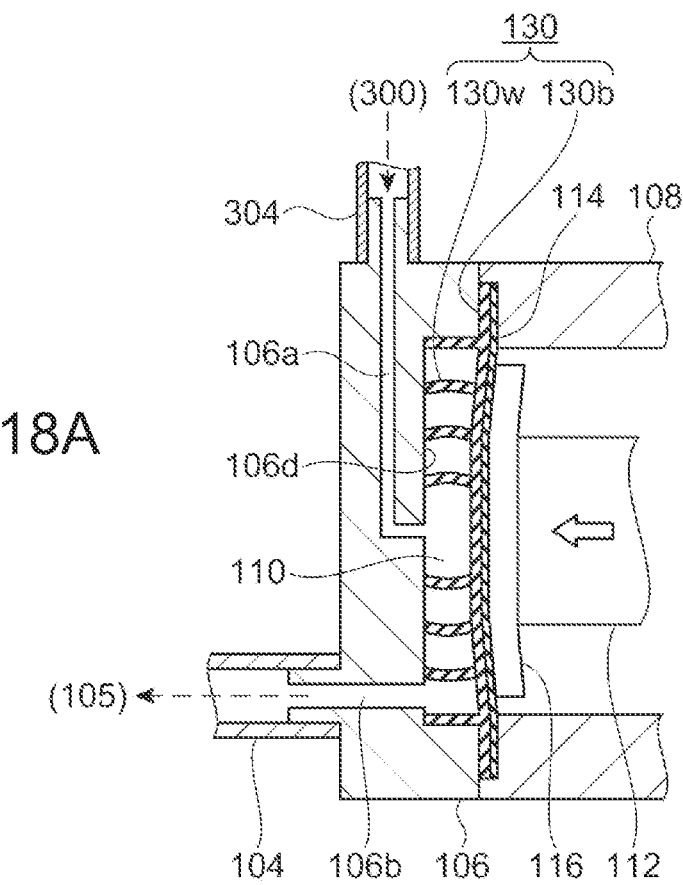
FIG. 18A is a partly cross-sectional view showing a state in which a drive voltage waveform is applied to the piezoelectric element in the sixth embodiment.
Figure 18B:
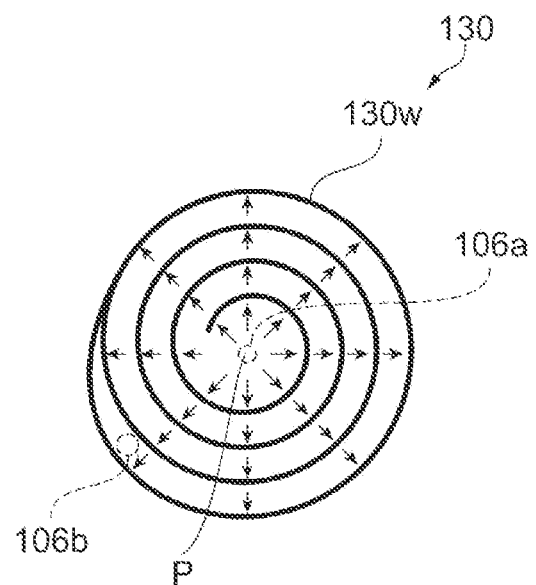
FIG. 18B is a plan view showing the shape of the flow channel forming member in a state in which the drive voltage waveform is applied to the piezoelectric element in the sixth embodiment.

FIG. 18A is a partly cross-sectional view of the pulsation generator 100 showing a state in which a drive voltage waveform is applied to the piezoelectric element 112 in the sixth embodiment, and FIG. 18B is a plan view of the flow channel forming member 130 in a state in which the drive voltage waveform is applied to the piezoelectric element 112 in the sixth embodiment. When the drive voltage waveform is applied to the piezoelectric element 112 in a state in which the liquid chamber 110 is filled with liquid, the piezoelectric element 112 is expanded by an increased drive voltage and presses the diaphragm 114 and the supporting panel 130b of the flow channel forming member 130 toward the liquid chamber 110 via the reinforcing plate 116 as shown in FIG. 18A. Consequently, the volume of the liquid chamber 110 is reduced, and the liquid in the liquid chamber 110 is pressurized. The liquid pressurized in the liquid chamber 110 in this manner is ejected from the nozzle 105 via the outflow channel 106b and the liquid ejecting tube 104 in a pulsed manner as shown by an arrow of a broken line in FIG. 18A.

Two channels, namely, the inflow channel 106a and the outflow channel 106b are connected to the liquid chamber 110. Therefore, the liquid pressurized in the liquid chamber 110 is considered to flow out not only from the outflow channel 106b, but also from the inflow channel 106a. However, since flowability of the liquid in the flow channel is determined by the cross-sectional area of the flow channel, the length of the flow channel, or the like, the liquid is allowed to flow out easier from the outflow channel 106b than from the inflow channel 106a by appropriately setting the cross-sectional areas or the lengths of the inflow channel 106a and the outflow channel 106b. For example, in the fifth embodiment, the diameter of the outflow channel 106b is on the order of 1 mm, and the inflow channel 106a has a capillary shape having a diameter on the order of 0.3 mm. Therefore, the backflow from the inflow channel 106a is inhibited.

Since there is a flow of liquid pumped out from the liquid supply unit 300 and urged to flow into the liquid chamber 110 at the inflow channel 106a, outflow of the liquid in the liquid chamber 110 can be prevented. In contrast, few elements which resist the outflow of the liquid in the liquid chamber 110 or increase the fluid inertia exist in the outflow channel 106b. Therefore, the liquid pressurized in the liquid chamber 110 exclusively flows out from the outflow channel 106b and is ejected from the nozzle 105 at the distal end thereof via the liquid ejecting tube 104.

The interior of the liquid chamber 110 in the sixth embodiment is partitioned into a spiral shape by the partitioning wall 130w of the flow channel forming member 130. However, when the volume of the liquid chamber 110 is reduced due to the extension of the piezoelectric element 112, the liquid in the liquid chamber 110 flows not only along the spiral-shaped partitioning wall 130w, but also toward the outer peripheral side of the liquid chamber 110 upon deformation of the partitioning wall 130w toward the outflow channel 106b on the outer peripheral edge portion. This point will be described as a postscript below.

First, when considering the partitioning wall 130w which constitutes the innermost part of the multiply wound spiral-shaped partitioning wall 130w, the inflow channel 106a is opened at the center portion of the liquid chamber 110 inside the innermost part of the partitioning wall 130w. Therefore, when the volume of the liquid chamber 110 is reduced, the liquid flows out from the outflow channel 106b and hence the pressure rise in the liquid chamber 110 is inhibited.

In contrast, since the inflow channel 106a has a capillary shape and inhibits the outflow of the liquid, the pressure rises more on the inside of the partitioning wall 130w than the outside of the partitioning wall 130w. Since the partitioning wall 130w is formed of a flexible material so as to be deformable, the liquid pushes the partitioning wall 130w from the inside under the higher pressure toward the outside under the lower pressure and deforms the same to reduce the pressure difference between the inside and the outside. Since the partitioning wall 130w in the sixth embodiment extends upright from the supporting panel 130b, and is secured at the distal end to the depression bottom 106d of the second case 106, the center portion of the partitioning wall 130w is deformed so as to bend outward by being pushed from the inside as shown in FIG. 18A.

The pressure difference between the inside and the outside of the partitioning wall 130w is generated not only around the innermost turn of the partitioning wall 130w, but also around the second innermost turn of the partitioning wall 130w due to the outward deformation of the innermost turn of the partitioning wall 130w and lowering of the inside pressure. This phenomenon propagates also to the third innermost turn of the partitioning wall 130w. Therefore, the spiral-shaped partitioning wall 130w is deformed as a whole toward the outside of the liquid chamber 110 so as to enlarge the spiral.

When the volume of the liquid chamber 110 is reduced due to the elongation of the piezoelectric element 112, the center portion of the spiral-shaped partitioning wall 130w is deformed so as to bend toward the outside of the liquid chamber 110, so that the liquid in the liquid chamber 110 is urged to move from the center portion of the liquid chamber 110 toward the outflow channel 106b of the outer peripheral edge portion as indicated by arrows of a broken line shown in FIG. 18B.

When the volume of the liquid chamber 110 is reduced by the expansion of the piezoelectric element 112, the liquid of an amount corresponding thereto is collected at the outflow channel 106b and then pushed out therefrom, so that the liquid is ejected from the nozzle 105 at the distal end of the liquid ejecting tube 104. At this time, it is also considered that a sufficient amount of liquid cannot be collected from the periphery to the outflow channel 106b at the outer peripheral edge portion by being hindered by the spiral-shaped partitioning wall 130w in the liquid chamber 110. However, in the pulsation generator 100 according to the sixth embodiment, the amount of displacement due to the expansion of the piezoelectric element 112 is small, and the amount of liquid ejected by one pulse (ejecting amount) is on the order of 1/100 of the volume of the liquid chamber 110. Therefore, a sufficient amount of liquid can be collected to the outflow channel 106b from the center portion by a slight deformation of the partitioning wall 130w toward the center of the liquid chamber 110. This can be proved by the expression (1) to the expression (4) described in the third embodiment.

As shown in FIG. 18A, the peripheral edge portion of the supporting panel 130b is fixed by being cramped between the first case 108 and the second case 106, and the outer diameter of the reinforcing plate 116 is smaller than the outer diameter of the supporting panel 130b, and the cross-sectional dimension of the piezoelectric element 112 is smaller than the outer diameter of the reinforcing plate 116. Therefore, when the liquid chamber 110 is pressed by the piezoelectric element 112, the outer peripheral edge is warped about the center portion where the inflow channel 106a is arranged. Therefore, the pressing amount against the liquid chamber 110 is large near the center portion, and hence the change in volume in this portion is large. In contrast, the pressing amount is small in the outer peripheral side, and hence the change in volume of the liquid chamber 110 is small in this area. In other words, the pressure in the liquid chamber 110 seems to be higher in the center portion and be decreased as it goes toward the outer peripheral portion. Therefore, the liquid in the liquid chamber 110 is pushed strongly from the center portion to the outer peripheral portion on the basis of the fact that the liquid is pumped at a substantially constant pressure from the liquid supply unit 300 to the inflow channel 106a.

Therefore, the pressure in the vicinity of the inflow channel 106a at the center portion is increased, and the returned pressure of the liquid to the inlet port 110a is increased correspondingly. However, since the inlet port 110a has a diameter of a capillary shape, the backflow from the liquid chamber 110 to the inflow channel 106a is inhibited. Therefore, the pressure in the liquid chamber 110 can be increased, and hence a strong liquid ejection is achieved.

In the sixth embodiment, the spiral flow channel is formed using the flow channel forming member 130, and the outflow channel 106b is communicated with the outer peripheral edge portion of the liquid chamber 110 formed into the spiral shape and the inflow channel 106a is communicated with the center portion of the liquid chamber 110. In this configuration as well, the concepts of the fourth embodiment or of the fifth embodiment described above may be applied.

Seventh Embodiment

The seventh embodiment is different from the fourth embodiment in the arrangement of the inflow channel 106a and the outflow channel 106b, and the similar configurations as the fourth embodiment may be applied as regards other points. Therefore, the same components as the fourth embodiment are denoted by the same reference numerals as the fourth embodiment, and detailed description of the common portions will be omitted.

Figure 19A:
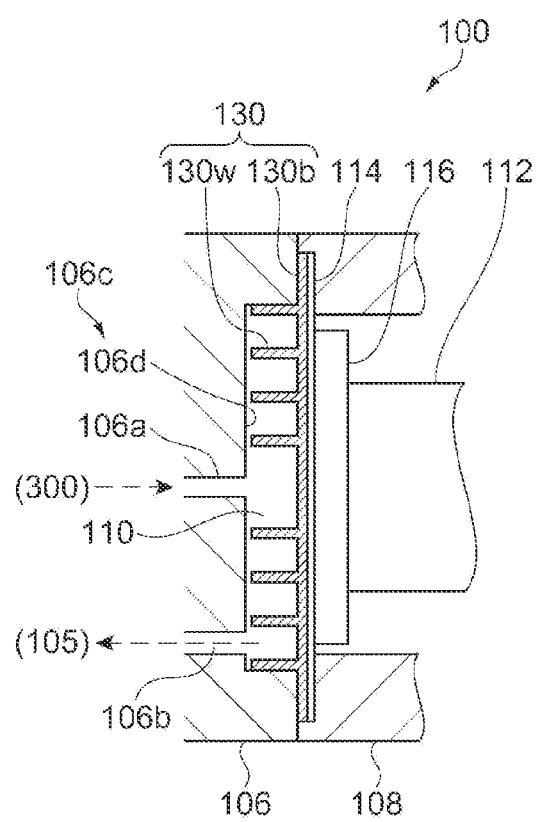
FIG. 19A shows part of an internal structure of a pulsation generator according to a seventh embodiment in a state in which a drive voltage waveform is not applied to the piezoelectric element.
Figure 19B:
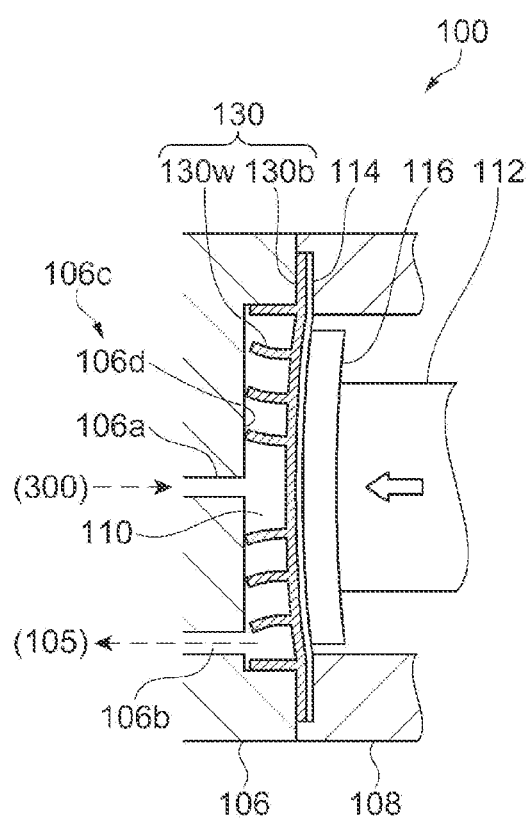
FIG. 19B shows part of the internal structure of the pulsation generator according to the seventh embodiment in a state in which the drive voltage waveform is applied to elongate the piezoelectric element.

FIG. 19A is an explanatory drawing of part of the internal structure of the pulsation generator 100 according to the seventh embodiment in a state in which a drive voltage waveform is not applied to the piezoelectric element 112, and FIG. 19B is an explanatory drawing of the internal structure of the pulsation generator 100 according to the seventh embodiment in a state in which the drive voltage waveform is applied to the piezoelectric element 112.

As shown in FIG. 19A, the flow channel forming member 130 is provided with the spiral-shaped partitioning wall 130w so as to extend upright from the supporting panel 130b. Formed in the interior of the liquid chamber 110 is a spiral flow channel partitioned by the partitioning wall 130w. In the seventh embodiment, the distal end of the partitioning wall 130w (opposing the second case 106) is not secured to the depression bottom 106d of the second case 106, and a small gap is provided between the distal end of the partitioning wall 130w and the depression bottom 106d. The outflow channel 106b is opened at the outer peripheral edge portion of the liquid chamber 110 formed into the spiral shape, and the inflow channel 106a is opened at the center portion of the liquid chamber 110.

In the seventh embodiment in this configuration, in the same manner as the fifth embodiment, the liquid flowed into the liquid chamber 110 from the inflow channel 106a (opened at the center portion thereof) flows to the outflow channel 106b at the center while turning along the partitioning wall 130w, whereby the liquid chamber 110 is filled with the liquid. Since the gap between the distal end of the partitioning wall 130w and the depression bottom 106d is very small, the liquid flowed into the liquid chamber 110 exclusively flows along the spiral flow channel.

When the piezoelectric element 112 is expanded by an application of a drive voltage waveform in a state in which the liquid chamber 110 is filled with the liquid in this manner, the volume of the liquid chamber 110 is reduced, and the liquid in the liquid chamber 110 is pressurized. At this time, since a pressure difference is generated between the inside and the outside of the partitioning wall 130w, the partitioning wall 130w is pressed from the inside with a higher pressure to the outside with a lower pressure and hence is deformed. According to the seventh embodiment, since the distal end of the partitioning wall 130w is not secured to the depression bottom 106d of the second case 106, the distal end side of the partitioning wall 130w is deformed so as to incline toward the outer peripheral side of the liquid chamber 110 as show in FIG. 19B.

In this manner, when the distal end side of the partitioning wall 130w is inclined toward the outer peripheral side of the liquid chamber 110, the liquid on the inside of the partitioning wall 130w flows into the outer peripheral side beyond the partitioning wall 130w. Therefore, a flow of the liquid flowing toward the outflow channel 106b on the outer peripheral side across the spiral flow channel is generated in the interior of the liquid chamber 110.

As described thus far, in the pulsation generator 100 according to the seventh embodiment, the distal end of the partitioning wall 130w is not secured to the depression bottom 106d of the second case 106, but when the liquid chamber 110 is filled with the liquid, the flow of the liquid in the liquid chamber 110 can be restricted to a constant flow velocity along the spiral flow channel formed by the partitioning wall 130w in the same manner as the fifth embodiment described above. Therefore, accumulation of air bubbles at a portion in which the flow of liquid is slow is avoided, and the air bubbles in the liquid chamber 110 can be discharged quickly.

Also, when the piezoelectric element 112 is expanded and the volume of the liquid chamber 110 is reduced, the distal end of the partitioning wall 130w which is not secured to the depression bottom 106d of the second case 106 falls toward the outer periphery of the liquid chamber 110, whereby the liquid flowing toward the outflow channel 106b at the center beyond the partitioning wall 130w is generated in the interior of the liquid chamber 110. In this manner, since the liquid is collected to the outflow channel 106b at the center from the periphery together with the flow flowing across the spiral flow channel, the liquid can be ejected adequately.

Eighth Embodiment

Subsequently, the configuration of the pulsation generator 100 according to an eighth embodiment will be described.

The eighth embodiment is different from the fifth embodiment in the arrangement of the inflow channel 106a and the outflow channel 106b, and the similar configurations as the fifth embodiment may be applied as regards other points. Therefore, the same components as the fifth embodiment described above are denoted by the same reference numerals as the fifth embodiment, and detailed description of the common portions will be omitted.

Figure 20A:
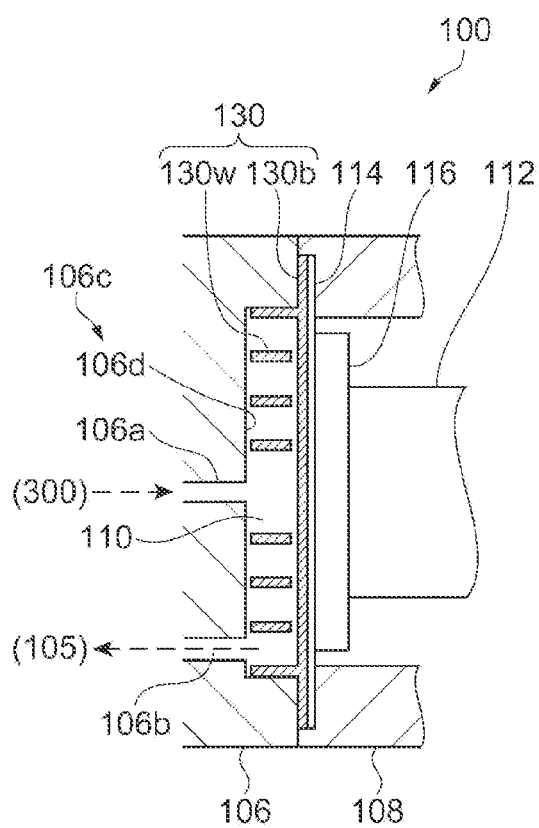
FIG. 20A shows part of an internal structure of a pulsation generator according to an eighth embodiment in a state in which a drive voltage waveform is not applied to the piezoelectric element.
Figure 20B:
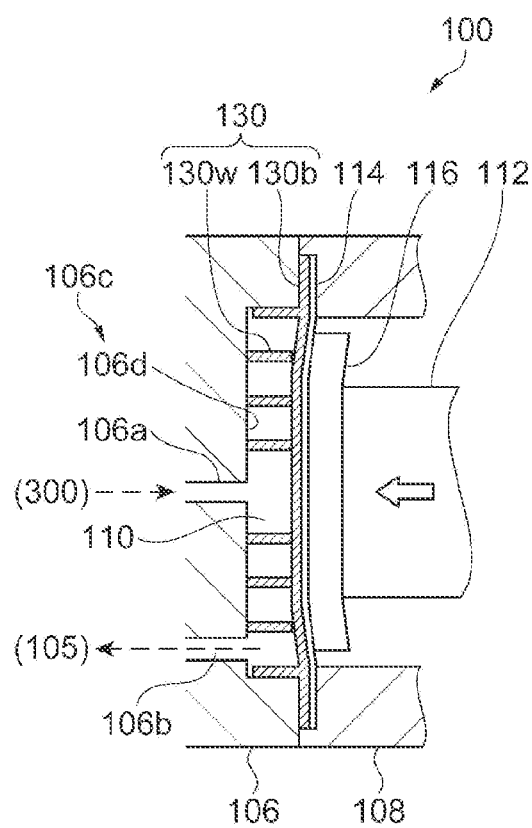
FIG. 20B shows part of the internal structure of the pulsation generator according to the eighth embodiment in a state in which the drive voltage waveform is applied to the piezoelectric element.

FIG. 20A is an explanatory drawing of the internal structure of the pulsation generator 100 according to the eighth embodiment in a state in which a drive voltage waveform is not applied to the piezoelectric element 112. FIG. 20B is an explanatory drawing of the internal structure of the pulsation generator 100 according to the eighth embodiment in a state in which the drive voltage waveform is applied to elongate the piezoelectric element 112. As shown in FIG. 20A, in the pulsation generator 100 according to the eighth embodiment, the spiral flow channel (divided by the spiral-shaped partitioning wall 130w) is formed in the interior of the liquid chamber 110 in the same manner as the fifth embodiment described above.

The partitioning wall 130w is not secured to the depression bottom 106d of the second case 106, and a small gap is provided with respect to the depression bottom 106d. The partitioning wall 130w does not extend entirely upright from the supporting panel 130b. Only a portion of the multiply wound spiral partitioning wall 130w which constitutes the outermost tern extends upright from the supporting panel 130b, and the remaining inner peripheral portion does not extend upright from the supporting panel 130b and has a small gap therefrom although having a continuous spiral shape.

In the eighth embodiment in this configuration, the liquid flowed into the liquid chamber 110 from the inflow channel 106a opened at the center portion thereof flows to the outflow channel 106b at the outer peripheral edge portion while turning along the partitioning wall 130w, whereby the liquid chamber 110 is filled with the liquid. Since the gap between the distal end of the partitioning wall 130w and the depression bottom 106d and the gap between the distal end of the partitioning wall 130w and the supporting panel 130b are very small, the liquid flowed into the liquid chamber 110 exclusively flows along the spiral flow channel.

In the pulsation generator 100 according to the eighth embodiment in this manner as well, when the liquid chamber 110 is filled with the liquid, the flow of the liquid in the liquid chamber 110 is restricted to a constant flow velocity along the spiral flow channel formed by the partitioning wall 130w, the air bubbles in the liquid chamber 110 can be discharged quickly.

In contrast, as shown in FIG. 20B, when the volume of the liquid chamber 110 is reduced by the expansion of the piezoelectric element 112 (and hence the pressure difference between the inside and the outside of the partitioning wall 130w occurs), the partitioning wall 130w is pressed from the inside with a higher pressure toward the outside with a lower pressure. At this time, the portion of the partitioning wall 130w on the inner peripheral portion which is not fixed to the depression bottom 106d and the supporting panel 130b is moved toward the outer periphery of the liquid chamber 110 as if a spring is released. Therefore, the pressurized liquid in the liquid chamber 110 is moved toward the outer periphery of the liquid chamber 110. In addition, a flow of the liquid toward the outflow channel 106b located in the direction of the outer periphery is generated so as to intersect the spiral flow channel beyond the partitioning wall 130w and hence the liquid is collected to the outflow channel 106b from the periphery, so that the liquid can be ejected strongly.

In the sixth to eighth embodiments described above, the inflow channel 106a is arranged at the center portion of the liquid chamber 110 and the outflow channel 106b is arranged at the outer peripheral portion of the liquid chamber 110. By arranging the inflow channel 106a and the outflow channel 106b in this manner, since the liquid is pumped from the center portion to the outflow channel on the outer peripheral portion, the capability of eliminating the air bubbles can further be enhanced.

In the third embodiment to the seventh embodiment described above, the spiral-shaped flow channel is formed by a partitioning wall 130w in the interior of the liquid chamber 110. However, the flow channel which is formed in the interior of the liquid chamber 110 is not specifically limited as long as it has a shape proceeding toward the outflow channel 106b while turning from the inflow channel 106a and, for example, a modification such as a zigzag pattern may be added.

The liquid ejecting apparatus 10 described thus far may be utilized as a surgical operation tool configured to incise or excise living tissues by ejecting liquid such as water or physiologic saline toward the living tissues, including: medical use such as application of medical solution to wounds or washing wounds, drawing using ink as liquid, washing of precise parts, or for a cooling apparatus of electronic apparatus by ejecting a small amount of the liquid with a high speed.

What is claimed is:

1. A liquid ejecting unit comprising:
a first case;
an actuator accommodated in the first case;
a second case configured to be connected to the first case, wherein the second case having a first recess which has an opening configured to be communicated with a liquid ejecting nozzle;
a first flexible member configured to be disposed between the first recess and the actuator; and
a second flexible member configured to be disposed between the first flexible member and the first recess,
wherein the first flexible member is configured to contact with the second flexible member.

2. The liquid ejecting unit according to claim 1, wherein the first flexible member is fixed to the first case, and the second flexible member is fixed to the second case,
wherein the second case is configured to detach from the first case.

3. The liquid ejecting unit according to claim 1, further comprising:
a liquid chamber configured to accommodate the liquid, wherein the liquid chamber is formed by the first recess and the second flexible member.

4. The liquid ejecting unit according to claim 1, wherein the first case having a second recess in which the first flexible member is disposed.

5. The liquid ejecting unit according to claim 4, wherein the second flexible member is disposed in the second recess.

6. The liquid ejecting unit according to claim 1, further comprising:
a plate member which is disposed between the first flexible member and the actuator.

7. The liquid ejecting unit according to claim 1, wherein the liquid is ejected from the nozzle when the first flexible member and the second flexible member are deformed by actuating of the actuator.

8. The liquid ejecting unit according to claim 1, wherein when the first case is connected to the second case, an edge portion of the first flexible member is contact with the first case and the second flexible member, and an edge of the second flexible member is contact with the second case and the first flexible member.

9. The liquid ejecting unit according to claim 8, wherein a part of the second flexible member is space apart from the second case when the first case is connected to the second case.

10. The liquid ejecting unit according to claim 1, wherein an inner diameter of the first recess is smaller than an outer diameter of the second flexible member.

11. The liquid ejecting unit according to claim 1, wherein a thickness of the second flexible member is different from a thickness of the first flexible member.

12. The liquid ejecting unit according to claim 11, wherein the thickness of the second flexible member is thicker than the thickness of the first flexible member.

13. The liquid ejecting unit according to claim 1, further comprising:
a third case being configured to contact with the actuator.

14. A liquid ejecting apparatus comprising:
a liquid supply unit which supply a liquid;
a nozzle which eject the liquid; and
a liquid ejecting unit according to claim 1.

* * * * *